(12) United States Patent
Dolan et al.

(10) Patent No.: US 11,773,399 B2
(45) Date of Patent: Oct. 3, 2023

(54) METHODS AND COMPOSITIONS FOR ENHANCING POLYPEPTIDE PRODUCTION

(75) Inventors: Maureen C. Dolan, Jonesboro, AR (US); Argelia Lorence, Jonesboro, AR (US); Giuliana Medrano, Jonesboro, AR (US)

(73) Assignee: Arkansas State University—Jonesboro, State University (AR)

( * ) Notice: Subject to any disclaimer, the term of this patent is extended or adjusted under 35 U.S.C. 154(b) by 945 days.

(21) Appl. No.: 13/503,473

(22) PCT Filed: Oct. 22, 2010

(86) PCT No.: PCT/US2010/053795
§ 371 (c)(1),
(2), (4) Date: Apr. 23, 2012

(87) PCT Pub. No.: WO2011/050286
PCT Pub. Date: Apr. 28, 2011

(65) Prior Publication Data
US 2012/0207707 A1 Aug. 16, 2012

Related U.S. Application Data

(60) Provisional application No. 61/254,522, filed on Oct. 23, 2009.

(51) Int. Cl.
| | | |
|---|---|---|
| C12N 15/82 | (2006.01) | |
| C12N 15/67 | (2006.01) | |
| C12P 21/02 | (2006.01) | |
| C07K 14/54 | (2006.01) | |

(52) U.S. Cl.
CPC ...... *C12N 15/8216* (2013.01); *C07K 14/5434* (2013.01); *C12N 15/67* (2013.01); *C12N 15/8257* (2013.01); *C12P 21/02* (2013.01)

(58) Field of Classification Search
CPC .................................................. C12N 15/79
See application file for complete search history.

(56) References Cited

U.S. PATENT DOCUMENTS

| | | | |
|---|---|---|---|
| 5,032,514 | A | 7/1991 | Anderson et al. |
| 7,635,592 | B2 | 12/2009 | West et al. |
| 2002/0100075 | A1* | 7/2002 | Conklin et al. ............ 800/278 |
| 2004/0133938 | A1* | 7/2004 | Dan ................. C12N 5/0025 800/278 |
| 2004/0152197 | A1 | 8/2004 | Gelvin et al. |
| 2007/0118916 | A1 | 5/2007 | Puzio et al. |
| 2007/0186308 | A1* | 8/2007 | Reuber et al. ............ 800/278 |
| 2008/0060093 | A1 | 3/2008 | Zieler et al. |
| 2008/0305531 | A1 | 12/2008 | Lam et al. |

FOREIGN PATENT DOCUMENTS

| | | |
|---|---|---|
| WO | WO 2000/036911 | 6/2000 |
| WO | WO 2002/050286 | 6/2002 |
| WO | WO 2004/061098 | 7/2004 |
| WO | WO 2006/104503 | 10/2006 |

OTHER PUBLICATIONS

Smirnoff, N. 1996. The Function and Metabolism of Ascorbic Acid in Plants. Annals of Botany 78: 661-669.*
Mittler, R. 2002. Oxidative stress, antioxidants and stress tolerance. Trends in Plant Science. vol. 7: 405-410.*
Conklin et al. 1999. Genetic evidence for the role of GDP-mannose in plant ascorbic acid (Vitamin C) biosynthesis. Proc. Natl. Acad. Sci. vol. 96: 4198-4203.*
V. Hausen, S. 1935. Effect of Vitamin C (Ascorbic Acid) on the Growth of Plants. Suomen Kemistilehti B, 5-6.*
Sigma-Aldrich Plant Tissue Culture Rotocols-Vitamin Mixtures, http://www.sigmaaldrich.com/life-science/molecular-biology/plant-biotechnology/tissue-culture-protocols/vitamin-mixtures.printerview.html.*
E.F. George et al. 2008. Plant propagation by Tissue Culture. Springer.*
Qiusheng et al. 2005. Effect of antioxidants on the plant regeneration and GUS expressive frequency of peanut explants by Agrobacterium tumefaciens. Plant Cell Tiss Organ Cult 81: 83-90.*
Jain et al. 2000. Metabolic engineering of an alternative pathway for ascorbic acid biosynthesis in plants. Molecular Breeding 6: 73-78.*
Woodard et al. 2003. Maize-derived bovine trypsin: characterization of the first large-scale, commercial protein product from transgenic plants. Biotechnol. Appl. Biochem 38: 123-130.*
Dan 2008. Biological functions of antioxidants in plant transformation. In Vitro Cell Dev Biol Plant. 44: 149-161.*
Smirnoff and Wheeler. 2000. Ascorbic Acid in Plants: Biosynthesis and Function. Critical reviews in biochemistry and molecular biology 35:291-314).*
Beryl. 2005. Getting started with tissue culture; media preparation, sterile technique, and laboratory equipment in Plant development and biotechnology, ed. R. Trigiano and D. Gray. CRC Press, pp. 24 and 25.*
Lee et al. 2007. Enhanced tolerance to oxidative stress in transgenic tobacco plants expressing three antioxidant enzymes in chloroplast. Plant Cell Rep 26: 591-598.*
Lee et al. 2006. Identification and deletion analysis of promoter of the pepper SAR8.2 gene activated by bacterial infection and abiotic stresses. Planta 224: 255-267.*
Mittler aned Zilinskas. 1994. Regulation of pea cytosolic ascorbate peroxidase and other antioxidant enxymes during the progression of drought stress and following recovery from drought. The Plant Journal 5: 397-405.*

(Continued)

*Primary Examiner* — Karen M Redden
(74) *Attorney, Agent, or Firm* — Quarles & Brady, LLP

(57) ABSTRACT

Methods of increasing production, stability or activity of a target polypeptide are provided herein. The method includes increasing the level of an antioxidant in a cell comprising a polynucleotide encoding the target polypeptide. Also provided are cells and transgenic organisms produced using the methods described herein. Methods of treating a subject with a condition treatable by administration of the target polypeptide are also disclosed. Finally methods and compositions for transiently increasing antioxidants in plant cells are provided.

11 Claims, 13 Drawing Sheets

(56) References Cited

OTHER PUBLICATIONS

Pallanca et al. 1999. The control of ascorbic acid synthesis and turnover in pea seedlings. Journal of Experimental Botany 51: 669-674.*

Flynn et al. 1990. *Theobroma cacao* L. : an axillary bud in vitro propagation procedure. Plant Cell. Tissue and Organ Culture 20: 111-117 (Year: 1990).*

Wang et al 2008. Expression of insect (*Microdera puntipennis dzungarica*) antifreeze protein MpAFP149 confers the cold tolerance to transgenic tobacco. Plant Cell Rep 2: 1349-1358. (Year: 2008).*

Wang et al. 2007. A protein extraction method compatible with proteomic analysis for the euhalophyte Salicornia europaea. Electrophoresis 28: 3976-3987. (Year: 2007).*

Enriquez-Obregon et al. 1999. Agrobacterium-mediated Japonica rice transformation: a procedure assited by an antinecrotic treatment. Plant cell, tissue and organ culture 59: 159-168. (Year: 1999).*

Burguieres et al. 2006. Effect of Vitamin C and folic acid on seed bigour response and phenolic-linked antioxidant activity. Science direct 98: 1393-1404. (Year: 2006).*

Shalata et al. 2001. Exogenous ascorbic acid increases resistance to salt stress and reduces lipid peroxidation. Journal of Experimental Botany 52: 2207-2211. (Year: 2001).*

Branduardi et al. 2007. Biosynthesis of Vitamin C by Yeast Leads to Increased Stress Resistance. PLoS One 2(10): e1092. doi: 10.1371/journal.pone.0001092 (Year: 2007).*

Enriquez-Obregon et al. 1997. Genetic transformation of sugarcane by Agrobacterium tumefaciens using antioidant compounds. Biotecnologia Aplicada 14: 169-174. (Year: 1997).*

Office Action dated Oct. 23, 2015 for European Patent Application No. 10825758.5 (5 pages).

Devi, R. et al., "Folate contents of some selected Fijian foods using tri-enzyme extraction method," (2008) Food Chemistry 106:1100-1104.

Jureviciute, I. et al., "Polyaniline-modified electrode as an amperometric ascorbate sensor," (2005) Sensors and Actuators 107:716-721.

Lisko, K.A. et al., "Engineering ascorbate for enhanced growth, nutritional content, and stress tolerance in crops," (2008) In Vitro Cellular and Development Biology-Animal 44:S28 (Abstract).

Van Eylen, D. et al., "Behavior of mustard seed (*Sinapis alba* L.) myrosinase during temperature/pressure treatments: a case study on enzyme activity and stability," (2008) Eur Food Res Technol 226:545-553.

Office Action dated Dec. 9, 2013 for European Patent Application No. 10825758.5 (5 pages).

Office Action dated Dec. 17, 2014 for European Patent Application No. 10825758.5 (6 pages).

Shamloul, M. et al., "Optimization and Utilization of *Agrobacterium*-mediated Transient Protein Production in *Nicotiana*" 2014 J. Vis. Exp. (86), e51204, doi:10.3791/51204.

Leuzinger, K. et al., "Efficient Agroinfiltration of Plants for High-level Transient Expression of Recombinant Proteins" 2013 J. Vis. Exp. (77), e50521, doi:10.3791/50521.

Smirnoff, N. "Ascorbate biosynthesis and function in photoprotection" 2000 Phil. Trans. R. Soc. Lond. B 355: 1455-1464.

Bánhegyi, G. et al., "Stress on redox," (2007) *FEBS Lett.* 581: 3634-3640.

Cheng, M. et al., "Invited review: Factors influencing agrobacterium-mediated transformation of monocotyiedonous species," (2004) In Vitro Cellular & Development Biology 40(1):31-45.

Corti, A. et al., "Cellular pathways for transport and efflux of ascorbate and dehydroascorbate," (2010) *Archives of Biochemistry and Biophysics* 500:107-115.

Eltayeb, A.E., "Overexpression of monodehydroascorbate reductase in transgenic tobacco confers enhanced tolerance to ozone, salt and polyethylene glycol stresses," (2006) *Planta: An International Journal of Plant Biology* 225(5):1255-1264.

Haynes, C.M. et al., "Degradation of misfolded proteins prevents ER-derived oxidative stress and cell death," (2004) *Molecular Cell* 15(5):767-776.

Joh, L.D. et al., "High-level transient expression of recombinant protein in lettuce," (2005) *Biotechnology and Bioengineering* 91(7)861-871.

Kapila, J. et al. "An *Agrobacterium*-mediated transient gene expression system for intact leaves," (1997) *Plant Sci* 122:101-108.

Lee, Y.-P. et al., "Enhanced tolerance to oxidative stress in transgenic tobacco plants expressing three antioxidant enzymes in chloroplasts," (2007) *Plant Cell Rep* 26:591-598.

Lorence, A. et al. "myo-Inositol Oxygenase Offers a Possible Entry Point into Plant Ascorbate Biosynthesis," (2004) *Plant Physiology* 134: 1200-1205.

Matringe, M. et al., "Tocotrienols, the unsaturated forms of Vitamin E, can function as antioxidants and lipid protectors in tobacco leaves," (2008) *Plant Physiology* 147(2):764-778.

Medrano, G. et al., "Rapid system for evaluating bioproduction capacity of complex pharmaceutical proteins in plants," In: "Recombinant Proteins from plants," *Methods and Protocols. Series: Methods in Molecular Biology* L. Faye, and V. Gomord, eds., (2009) Humana Press, Totowa, NJ, 483:51-67.

Medrano, G. et al., "Efficient plant-based production of chicken IL-12 yields a strong immunostimulatory cytokine," (2010) *J. Interferon Cytokine Res.* 30(3):143-153.

Radzio, J. et al., "L-Gulono-1,4-lactone Oxidase Expression Rescues Vitamin C Deficient *Arabidopsis* (*vtc*) Mutants," (2003) *Plant Molec. Biol.* 53: 837-844.

Raimondi, S. et al., "SOD1, a new *Kluyveromyces lactis* helper gene for heterologous protein secretion," (2008) *Appl. Environ. Microbiol.* 74(23): 7130-7137.

Sainsbury, F. et al. "Extremely high-level and rapid transient protein production in plants without the use of viral replication," (2008) *Plant Physiology* 148:1212-1218.

Schillberg, S. et al., "Opportunities for recombinant antigen and antibody expression in transgenic plants—technology assessment," (2005) *Vaccine* 23: 1764-1769; available online Nov. 2004.

Thordal-Christensen, H. et al., "Subcellular localization of $H_2O_2$ in plants. $H_2O_2$ accumulation in papillae and hypersensitive response during the barley-powdery mildew interaction," (1997) *The Plant Journal* 11:1187-1194.

Woitsch, S. et al., "Impact and interaction of lipophilic antioxidants in mutants and transgenic plants," (2005) *Journal of Plant Physiology* 162(11):1197-1209.

Xiao, Anfeng, et al., "Improvement of cell viability and hirudin production by ascorbic acid in Pichia pastoris fermentation," (2006) *Applied Microbiology and Biotechnology* 72(4):837-844.

Zhang, W. et al., "AMR1, an *Arabidopsis* gene that coordinately and negatively regulates the mannose/L-galactose ascorbic acid biosynthetic pathway." (2009) *Plant Physiology* 150:942-950.

International Search Report and Written Opinion of the International Searching Authority for Application No. PCT/US2010/053795 dated Dec. 27, 2010 (21 pages).

European Patent Office Search Report for Application No. 10825758.5 dated Mar. 13, 2013 (9 pages).

* cited by examiner

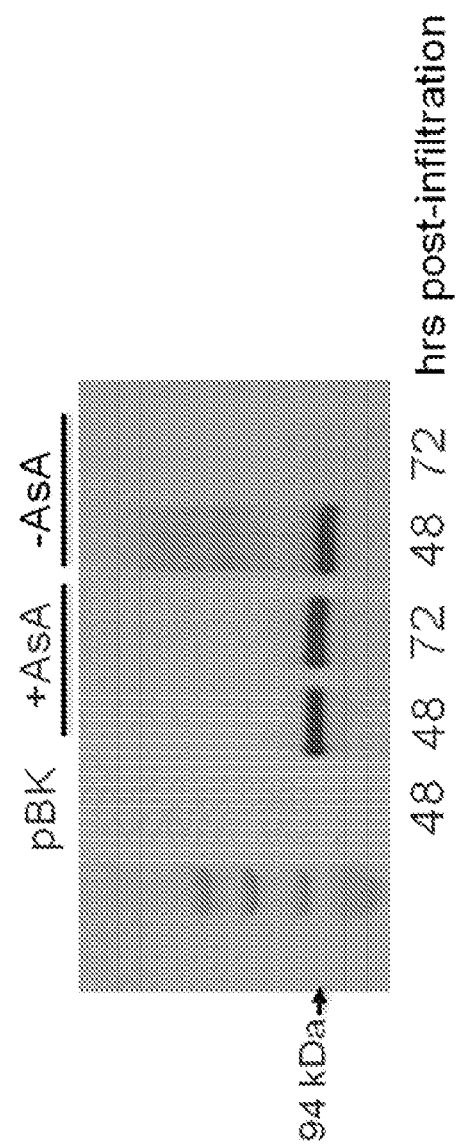

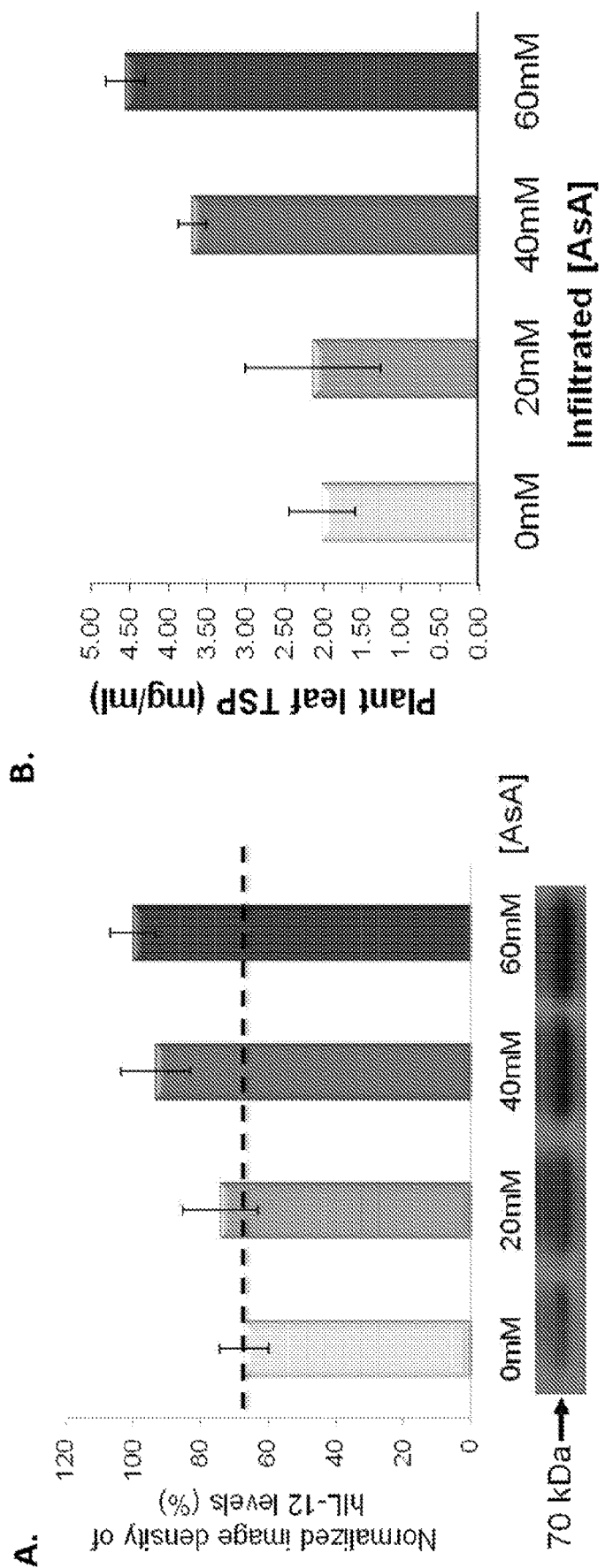

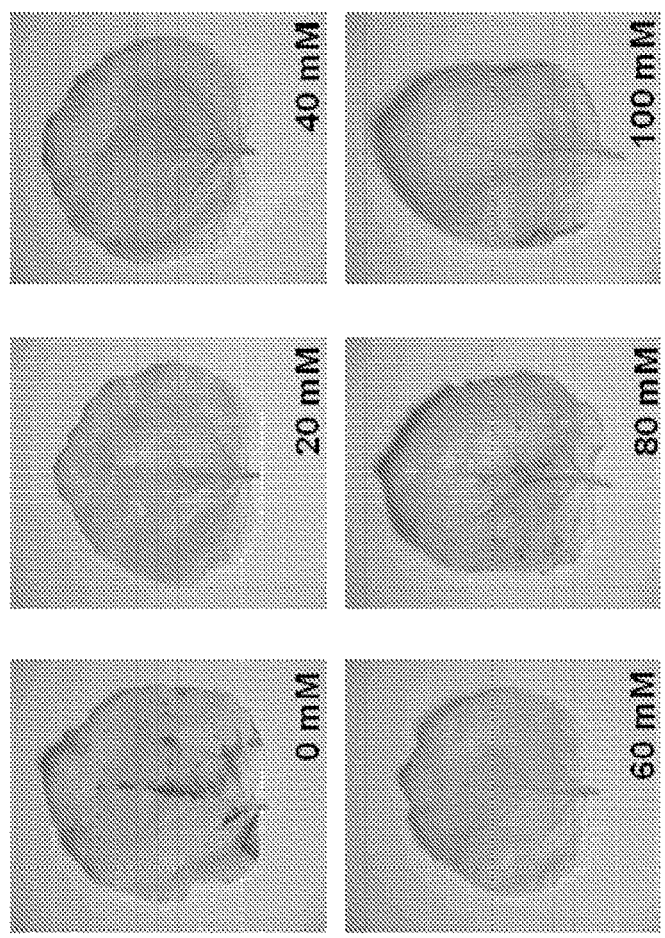
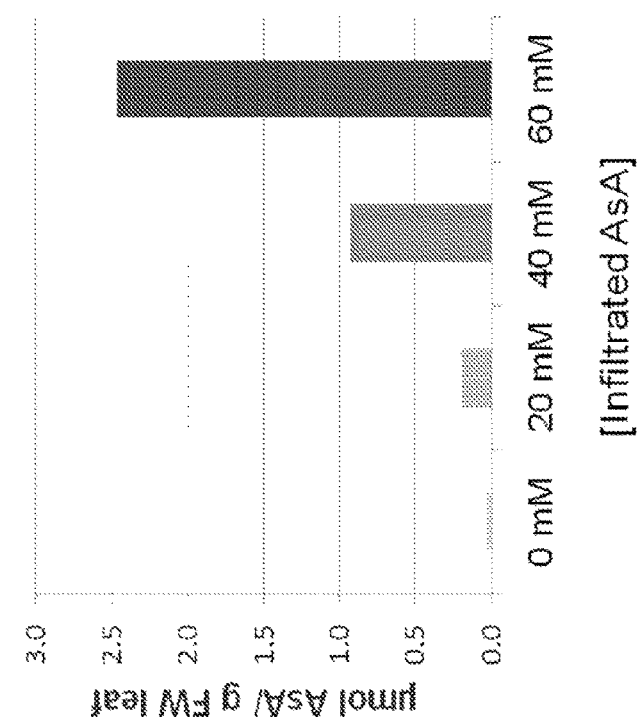
Figure 7

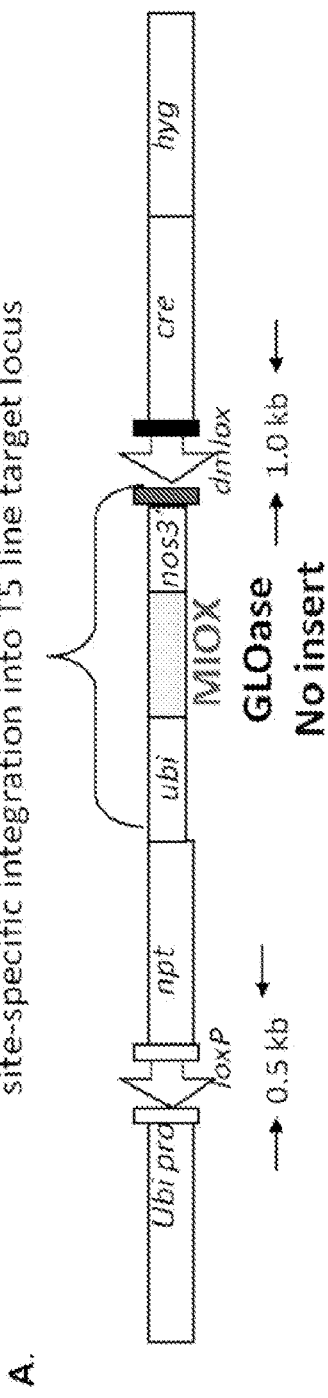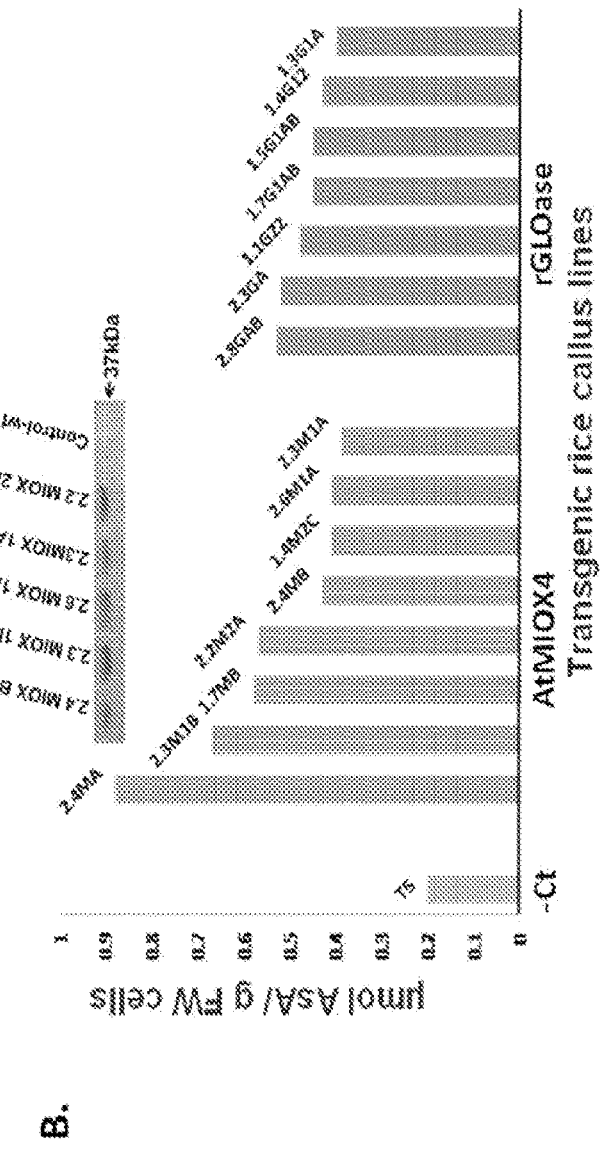
Figure 12

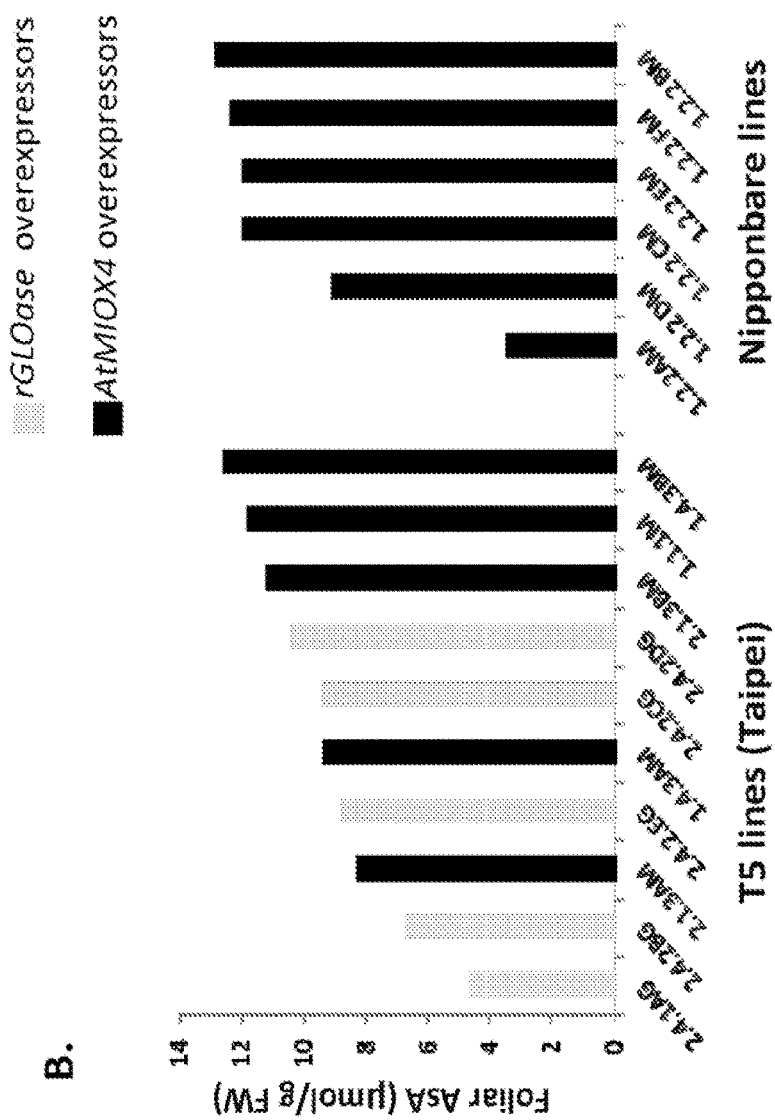
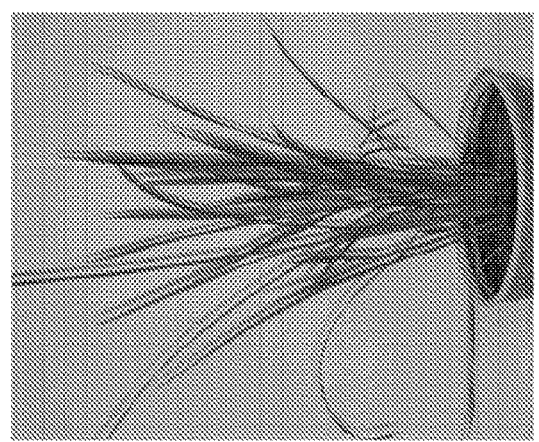
Figure 13

METHODS AND COMPOSITIONS FOR ENHANCING POLYPEPTIDE PRODUCTION

CROSS-REFERENCE TO RELATED APPLICATIONS

This patent application is a national stage filing under 35 U.S.C. § 371 of International Application No.: PCT/US2010/053795, filed Oct. 22, 2010, which claims the benefit of priority of U.S. Provisional Patent Application No. 61/254,522, filed Oct. 23, 2009, both of which are incorporated herein by reference in their entirety.

STATEMENT REGARDING FEDERALLY SPONSORED RESEARCH

This invention was made with government support under National Science Foundation grant number EPS 0701890. The government has certain rights in the invention.

INTRODUCTION

In recent years a large number of recombinant proteins with pharmaceutical, therapeutic or industrial potential have been identified. One limitation of bringing these recombinant proteins into commercial use is difficulties associated with expression of the protein from the recombinant host in large enough amounts to be useful. Many of the systems used for recombinant protein expression also require that the protein is purified prior to being used as a therapeutic. These steps are time-consuming, result in loss of protein and increase production costs. Therefore, new methods to further increase production and recovery of recombinant proteins from heterologous expression systems are needed.

SUMMARY

Methods for increasing production, stability or activity of a target polypeptide are provided herein. The methods include increasing the level of antioxidant in a cell comprising a polynucleotide encoding the target polypeptide under conditions that allow expression of the polypeptide. The cell increases production of the target polypeptide as compared to production of the polypeptide in a control cell. The stability and/or activity of the target polypeptide in the cells may also be increased as compared to the stability and activity of the target polypeptide produced in control cells.

In another aspect, cells including a first polynucleotide encoding a target polypeptide and a second polynucleotide encoding a second polypeptide capable of increasing antioxidants in the cell are disclosed. The production of the second polypeptide allows increased production of the target polypeptide as compared to cells not expressing the second polypeptide.

In still another aspect, methods of treating a subject with a condition are provided. The method includes administering the cells expressing increased target polypeptide to a subject with a condition treatable with the target polypeptide.

In still another aspect, methods of treating a subject with a condition include harvesting, isolating and/or purifying the target polypeptide from the cells expressing increased target polypeptide and administering the harvested target polypeptide to a subject with a condition treatable with the target polypeptide.

In a further aspect, methods of using the target polypeptide include harvesting the target polypeptide from the cells expressing increased target polypeptide to prepare a harvested target polypeptide and using the harvested target polypeptide in an assay.

In yet another aspect, methods for increasing the intracellular antioxidant levels via vacuum infiltration of a plant or plant cells with a media comprising at least one antioxidant are provided. Compositions suitable for vacuum infiltration of antioxidants are also provided.

BRIEF DESCRIPTION OF THE DRAWINGS

FIG. 5 is a photograph of a Western blot showing expression of a human glycoprotein at 48 and 72 hours post-transformation with or without the addition of vitamin C.

FIG. 6A is a photograph of a Western blot and semi-quantitative densitometry analysis showing the impact of co-infiltrated vitamin C dose on hIL-12 protein levels in the plant transient expression system.

FIG. 6B depicts a bar graph showing a dose-dependent effect of vitamin C increases the total soluble protein levels in 48 h post-infiltrated plant leaves.

FIG. 7A depicts a dose-dependent effect of infiltrated vitamin C on the total in planta foliar vitamin C concentrations of transient system host plants.

FIG. 7B is a set of photographs showing the dose-dependent effect of infiltrated vitamin C on in situ hydrogen peroxide levels in transient system host plants.

FIG. 12A depicts the expression cassettes encoding the *Arabidopsis* MIOX4 or rat L-gulono-1,4-lactone oxidase (GLOase) transgenes that were inserted into the T5 locus of a rice cell line using a Cre-loxP mediated integration strategy.

FIG. 12B is a graph showing the increased vitamin C content of the rice cell lines and a Western blot analysis showing a corresponding increase in the levels of the MIOX4 polypeptide in select rice cell lines.

FIG. 13 is a graph showing the increased vitamin C content of transgenic rice lines in two rice backgrounds (Taipei and Nipponbare) overexpressing MIOX4 or rGLOase genes (FIG. 13B) and a photograph showing the developmental stage of a rice plant transformant at which vitamin C content in planta was measured (FIG. 13A).

DETAILED DESCRIPTION

Figure 1:
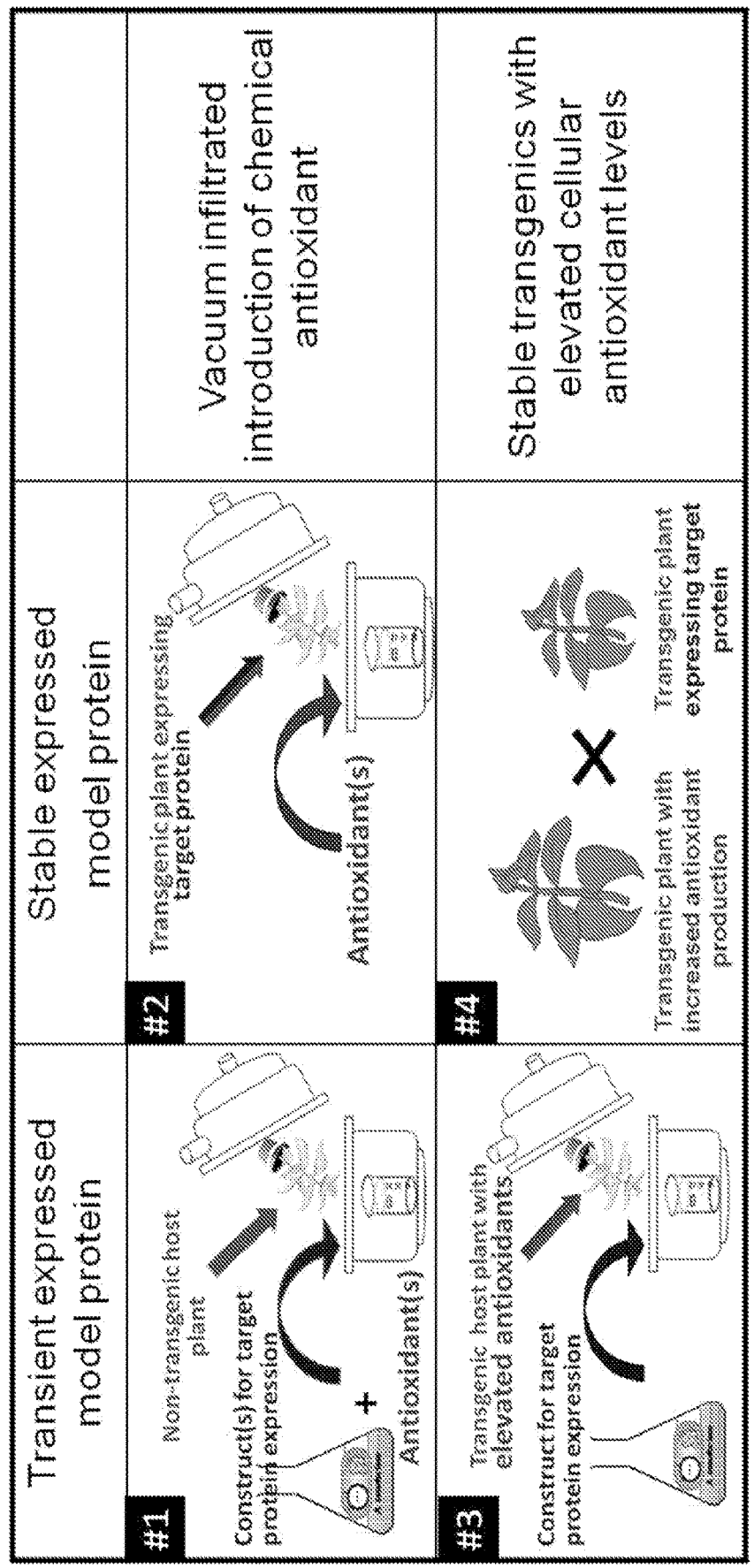
FIG. 1 depicts the four general embodiments wherein the increase of antioxidants in the bioproduction system leads to enhanced recombinant protein production yin plants.

The inventors have discovered that elevating intracellular levels of vitamin C, an antioxidant, in situ increases the stress tolerance and lowers the level of reactive oxygen species (ROS) in plants as well as other cell types. See U.S. patent application Ser. No. 11/908,551. As demonstrated in the examples, the inventors have further discovered that increased antioxidant levels within a cell results in increased production, stability and activity of recombinant non-native polypeptides. Thus, methods for increasing production, stability or activity of a target polypeptide are disclosed. The methods include increasing the level of an antioxidant in a cell expressing a target polypeptide such that the production, stability and/or activity of the target polypeptide is increased as compared to that in a control cell.

The target polypeptide may be any polypeptide including those having potential therapeutic, pharmaceutical, nutraceutical or industrial utility. Target polypeptides are generally non-native polypeptides, but may also be native polypeptides expressed recombinantly. Target polypeptides may be from a heterologous cell type and may be expressed by the cell either transiently or via a transgene stably integrated into the expression host genome. Target polypeptides include, but are not limited to an antibody, an interleukin, a growth factor, a cytokine, an enzyme or a therapeutic polypeptide.

The target polypeptide may be any polypeptide of interest capable of being expressed in the cell. Suitably the target polypeptide is a non-native polypeptide. For example, the target polypeptide may be a non-native or foreign (heterologous) protein such as, human interleukin-12 ("hIL-12"), mouse interleukin-12 ("mIL-12"), chicken interleukin-12 ("chIL-12"). The protein of interest or target polypeptide may be over-expressed using a recombinant expression system, such as a plant-based recombinant expression system. For increasing the biosynthesis of IL-12, the medium infiltrated into the plant (for intake into its cells) may include *A. tumefaciens* with IL-12:pBK as used in the examples.

Due to the ability to express larger quantities of these target polypeptides in more complex cellular systems such as plant or animal cells, polypeptides which require post-translational modifications for activity can be produced for commercial use by the methods described herein. Post-translational modifications may include, but are not limited to, protease cleavage, carbonylation, glycosylation, myristoylation, phosphorylation, formation of disulfide bonds, carbamoylation, acetylation, ubiquitination, citrullination, sumolation, and palmitoylation. Post-translation modifications may be required for correct protein folding, activity and stability.

The examples were completed in plants and plant cells, but similar results are expected in other cell types, including but not limited to bacteria, fungi, algae, yeast, insects or mammalian cells. Multi-cellular systems or organisms including, but not limited to, insects or non-human mammals, such as mice, may also be used in the methods. Tissues, organs or cell cultures derived from multi-cellular organisms including, but not limited to, insect cells, plant cells, callus, or organs, mammalian cells or tissues, may also be used in the methods. Both monocot and dicot cells and plants may be used in the methods described herein. Useful plants include, but are not limited to *Nicotiana* spp., including but not limited to, *Nicotiana benthamiana*, *Nicotiana tabaccum*, *Nicotiana excelsior*, as well as *Arabidopsis thaliana*, or other host plant species capable of intaking induction medium containing an antioxidant in addition to a polynucleotide encoding the target polypeptide. Plants useful in the methods may also include rice, corn, flax, lettuce, duckweed, tomato, carrot, soy, safflower, or other grains or oilseeds. These plants can be grown in plant chambers, growth rooms, green house, hydroponically, or as a field crop. Leaves can be collected at any point during growth that is optimal for the expression of the target polypeptide.

Examples of animal cell-based systems include, but are not limited to, Chinese hamster ovary (CHO) cells; mouse myelomas (NS0 and SP2/0); baby hamster kidney (BHK-21) cells; and human embryonic kidney (HEK-293) cells. Other eukaryotic cell-based systems include, for example, yeast (e.g., *Saccharomyces cerevisiae* and *Pichia pastoris*), other fungi and insect (e.g. *Spodoptera frugiperda* isolates Sf9 and Sf21; *Trichoplusia ni; Drosophila*) cells. Examples of prokaryote-based systems include, but are not limited to, bacteria such as *Escherichia coli*, *Salmonella*, *Lactobacillus*, *Bacillus* and *Klebsiella*.

The cells may be stably transformed such that the polynucleotide encoding the target polypeptide is incorporated into the genome such as the nucleus or plastid of a plant or plant cell. Alternatively, the cells may be transiently transformed or transfected such that polypeptide expression can be mediated by a viral vector, plasmid or an *Agrobacteria*-infiltration in a plant or plant cell. Methods of stably or transiently expressing target polypeptides in a wide variety of cells are well known to those skilled in the art. Expression vectors allowing for constitutive or inducible expression of target polypeptides are also well known to those skilled in the art and will largely depend on the cell type, species and polypeptide chosen. Such experimentation is well within the skill level of those in the art.

For transient transformation, methods known to those of skill in the art including, but not limited to, vacuum infiltration, liposome mediated delivery, transfection, temperature (heat) shock, particle bombardment, electroporation, reversible membrane permeabilization, microinjection, viral protein fusions (such as VP22) or other chemical or mechanical transformation or transfection methods may be used. One preferred bacterial strain for transformation of plants is the *A. tumefaciens* strain LBA4404 harboring the disarmed Ti plasmid pAL4404 bearing the vir region and streptomycin selectable marker, although any appropriate strain may be used. Alternative strains of *A. tumefaciens* have been used for transient and stable expression including, but not limited to, EHA105, EHA101, GV3101, AGL1 and AGLO with the appropriate antibiotic requirement for the *A. tumefaciens* strain used. The target polynucleotide may be inserted within the T-DNA region of a plant transformation vector. One useful transformation vector is the pBIB-Kan plant binary expression vector, however, other expression cassette systems familiar to those skilled in the art can be substituted. It may also be advantageous to construct the proper negative control strain for transient assay (e.g., *A. tumefaciens* LBA4404 transformed with the pBIB-Kan "empty" vector). In the examples the vectors were introduced into the cell using a vacuum infiltration method similar to that described by Medrano et al., 2009. Similar methods can be used to stably integrate the polynucleotide into the genome of the host cell. For example, viral integration sequences can be added to the target polynucleotide vector, the vector can be prepared for homologous recombination into the genome; transposons, Cre-loxP mediated integration or particle bombardment using biolistic-based delivery may also be used.

Antioxidants or derivatives thereof include any substance capable of slowing or preventing the oxidation of molecules, especially in intracellular reactions, including but not limited to water soluble, lipophilic and/or enzymatic antioxidants. Examples of antioxidants include, but are not limited to, vitamin C (ascorbic acid, ascorbate and AsA), vitamin E, vitamin D and vitamin K and any of their derivatives and glutathione. Derivatives include more or less stable forms of these antioxidants with varying solubility such as ascorbyl palmitate, magnesium ascorbyl phosphate and tetrasubstituted lipophilic ascorbates. Additional antioxidants that may be suitable for use in the methods include, but are not limited to, lipoic acid, uric acid, carotenes, coenzyme Q, melatonin, polyphenols, superoxide dismutase mimetics, catalase mimetics or peroxidase mimetics (i.e. mimetics include catalytic or enzymatic antioxidants similar to those found in the host cell). Combinations of antioxidants may be used as well. In particular, the Examples demonstrate that combination of a water-soluble (vitamin C) and a lipophilic (vitamin E) antioxidant may result in additional increases in protein production, stability or activity. Such a combination may have additive, more than additive or synergistic effects.

The levels of antioxidants in the cell may be increased in several ways. First, many cells are able to transport some antioxidants or their derivatives across the cell membrane such that addition of the antioxidant to the media in which the cells are grown is sufficient to increase the intracellular levels of the antioxidant and allow for increased target polypeptide production.

Alternatively, the antioxidants may be introduced directly into the cell using a transient infiltration or delivery system resulting in a non-permanent increase in antioxidants within the cell. For example, the antioxidants may be directly introduced into cells via methods available to those of skill in the art, including but not limited to, vacuum infiltration, liposome mediated delivery, transfection, sonication, temperature (heat) shock, particle bombardment, electroporation, reversible membrane permeabilization, microinjection, viral protein fusions (such as VP22) or other chemical or mechanical transformation or transfection methods. Many of these methods are similar to those used to incorporate a polynucleotide into a cell. In two of the embodiments depicted as #1 and #3 in FIG. 1, a transient plant infiltration method using a regulated vacuum pump was employed. This method enabled rapid and effective delivery of antioxidants into plant cells. Vacuum infiltration of plants has been used in the delivery of viral and bacterial based expression vectors for the purpose of protein production in a variety of host plants (Kapila et al., 1997; Joh et al., 2005; Schillberg et al., 2005; Sainsbury and Lomonossoff, 2008). The details of the vacuum infiltration method are outlined in a recent review (Medrano et al., 2009). Modifications were made to accommodate the delivery of antioxidants as outlined in the examples.

Cellular levels of antioxidants may also be increased using genetic engineering methods. These methods may result in increased antioxidant biosynthesis, increased recycling of oxidized antioxidants or decreased degradation. As shown in the Examples, increasing expression of an enzyme involved in the biosynthetic pathway of vitamin C, such as MIOX or GLOase results in increased synthesis of vitamin C in the plant. Similarly, it is expected that increased expression of other enzymes in the biosynthetic pathway of vitamin C and/or other antioxidants would also result in increased synthesis of the antioxidant. Additionally, overproduction of enzymes involved in recycling oxidized antioxidants is expected to result in increased levels of antioxidants and thus increased production, stability and/or activity of the target polypeptide. Finally, decreasing expression of a negative regulator of the biosynthetic pathway of an antioxidant may also be a means of increasing the levels of antioxidant in the cell.

Increased cellular levels of such, enzymes may be achieved using either transient or stable transfection/transformation systems similar to those discussed above for the target polypeptides. The enzymes targeted for overproduction may be involved in any of the biosynthetic pathways leading to antioxidant synthesis including, but not limited to, the mannose-galactose pathway, the galacturonate pathway, the gulose pathway and the myo-inositol pathway. Suitable enzymes involved in the biosynthesis of vitamin C include, but are not limited to, phosphomannose isomerase (PMI) 1 or 2, phosphomannose mutase (PMM), GDP-D-mannose pyrophosphorylase (VTC1), GDP-D-mannose-3,5-epimerase (GME), GDP-L-galactose phosphorylase (VTC2 or 5), L-galactose-1-phosphate phosphatase (VTC4), L-galactose-dehydrogenase (GalDH), L-galactono-1,4-lactone dehydrogenase (GLDH), methyl esterase, D-galacturonate reductase, aldono-lactonase, phytase, myo-inositol oxygenase (MIOX) 1-5, glucuronic acid reductase (GlcUR), gulonolactonase (GNL), and L-gulono-1,4-lactone oxidase (GLOase). Vitamin C can in addition be manipulated by over-expressing the following recycling enzymes: mono dehydroascorbate reductase (MDAR), and dehydroascorbate reductase (DHAR). A protein that has been shown to regulate multiple biosynthetic enzymes involved in vitamin C synthesis is "ascorbic acid mannose pathway regulator 1" (a.k.a. AMR; Zhang et al., 2009). Notably, AMR1 is a negative regulator of vitamin C biosynthesis such that knocking the gene encoding this enzyme out or otherwise interfering with synthesis of the polypeptide using an RNAi or other gene silencing approach would be expected to result in increased vitamin C production in the cell. Pathways and enzymes involved in biosynthesis of other antioxidants are known to or can be identified by those skilled in the art.

For the purpose of the methods described herein the antioxidant levels in the cells should be increased relative to those in a control cell. The level of antioxidants should be increased to a level that does not result in severe toxicity to the cell or the organism or tissue comprising the cell. In the examples, vitamin C was shown to increase target polypeptide production, stability and activity when added to cells at levels between 2 and 60 mM. At 80 and 100 mM in the plants tested vitamin C levels became detrimental to the cells (as shown by necrosis in FIG. 7B). Thus vitamin C is likely effective if 0.1 mM to 80 mM vitamin C is added to the cells, suitably at least 0.1 mM, 0.5 mM, 1 mM, 2 mM, 5 mM, 10 mM, 20 mM or 40 mM is added. Suitably less than 100 mM, 80 mM or 60 mM is added. While at 1000-fold less concentration and in the μM concentration range, the lipophilic antioxidant, vitamin K showed similar dose kinetics as vitamin C (see FIG. 8B). Vitamin K was shown to increase target polypeptide production and stability when added to cells at levels between 10 μM and 50 μM. At 100 μM, vitamin K was shown to become detrimental to the cells. Vitamin E showed a similar effective dose range as vitamin K in the μM scale but with slightly different dose kinetics than vitamins C and K as shown in the examples (see FIG. 8A). Based on lipophilic vitamin concentrations shown in examples, suitably at least 0.1 μM, 0.5 μM, 1 μM, 2 μM, 5 μM, 10 μM, 20 μM, 40 μM or 50 μM and suitably less than 55 μmM, 60 μM, 70 μM, 80 μM or 100 μM of the lipophilic antioxidants are used.

As shown in FIG. 1, the increased production of the target polypeptide may be achieved using at least four distinct methods encompassed by the teachings herein. One methodology depicted in FIG. 1, #1 involves introducing the antioxidants directly into the cells using a transient method and using a transient method to deliver the polynucleotide encoding the target polypeptide to the cell. In this embodiment the antioxidant and the polynucleotide encoding the target polypeptide may be introduced into the cell together, i.e. via the same process, or the polynucleotide may be introduced prior to or after the antioxidant.

A second methodology also shown in FIG. 1 #2 involves introducing the antioxidants directly into the cell as above by using methods such as vacuum infiltration techniques to allow intake medium containing an antioxidant into cells or multi-cellular systems or organisms, such as transgenic plants. In this embodiment, the cells have been genetically engineered to express the target polypeptide, such as interleukin-12 (or an elevated level thereof). The polynucleotide encoding the target polypeptide may be integrated into the cell's genome or may be stably carried by the cell on a non-genomic construct such as a plasmid or an artificial chromosome.

A third methodology shown in FIG. 1 #3 involves using cells genetically engineered to produce elevated intracellular levels of antioxidants. Suitable host cells or multi-cellular systems such as plants genetically engineered to express increased levels of polypeptides involved in the antioxidant biosynthetic pathway and that produce elevated levels of antioxidants as compared to cells that do not overexpress the polypeptides. In this embodiment, like in #1, the polynucleotide encoding the target polypeptide is introduced into the cell transiently.

A fourth embodiment shown in FIG. 1 #4 involves obtaining a cell genetically engineered to express increased levels of antioxidants and also to express the target polypeptide stably. One way to accomplish this method is by cross-breeding two groups of the same species of transgenic plant or animal, one group engineered for expressing elevated antioxidant levels and one group engineered for expressing the target polypeptide. The resulting population should have individuals expressing increased levels of the antioxidant and carrying the target polynucleotide such that increased levels of the target polypeptide are produced.

In the methods depicted as #1 and #2, the antioxidant may be increased by introducing the antioxidant itself into the cells directly. In the examples this was accomplished by vacuum infiltration of a chemical antioxidant, such as vitamin C, directly into the cells of the plant. Those of skill in the art will appreciate that the method chosen to introduce the antioxidant into the cell will depend on the type of cell and whether the cell is part of a multi-cellular system or organism. Alternatively, a polynucleotide encoding a polypeptide capable of increasing the antioxidant levels in a cell by increasing antioxidant production, recycling or limiting degradation may also be introduced and expressed transiently in the cell.

In the methods depicted in #3 and #4, the levels of antioxidant in the cell are increased by generating stable cell lines or transgenic organisms that possess increased antioxidants in the cells. In the examples this was accomplished by over-expressing polypeptides in the vitamin C biosynthetic pathway, such as MIOX or GLOase. The vitamin C biosynthetic pathway is known to those of skill in the art, such that other polypeptides involved in the pathway may be over-expressed (or under-expressed if the polypeptide is a negative regulator) to achieve increased levels of antioxidant in the cell.

To assess the levels of antioxidants and target polypeptides produced in a cell the methods outlined in the examples may be used. Those of skill in the art will also be able to use alternative methods. In the examples, typically leaves were harvested at 48, 72, and 96 h post-infiltration dependent upon the specific expression kinetics of each given target polypeptide and stored at −80° C. for subsequent qualitative and quantitative analyses. The frozen leaf tissue was ground by mortar and pestle with liquid nitrogen and extracted for either protein or ascorbate (vitamin C) analyses. An initial test to quickly assess and compare the impact of various antioxidants on protein production was completed by extracting protein from the leaves using a standard. SDS extraction buffer (Medrano et al., 2009) that solubilized all proteins. Samples were then resolved by SDS-PAGE (run under denaturing and reducing conditions) and Western immunoblotting analysis performed for the given target polypeptide. For example the expression of hIL-12 required primary antibody anti-human IL-12 (1:1000 v/v; R&D Systems) and secondary antibody anti-goat g alkaline phosphatase conjugated (1:10,000 v/v; BIORAD®) used in combination with a standard chemiluminescent detection agent to visualize hIL-12 expression levels. Densitometry using the BIORAD® VERSDOC4000™ and QUANT-1® software package was employed is establishing relative protein expression of the target polypeptide in evaluating the impact of antioxidants on its expression in plants. Alternatively, plant leaf tissues were extracted in standard physiological extraction buffers such as phosphate buffer saline (PBS) to maintain protein conformation for in vitro analyses including determining total soluble protein (TSP) of each sample (typically using a standard Bradford-based assay), ELISA-based methods (see below) and purification of target polypeptide.

In the case of in planta vitamin C analysis, leaf tissues from a defined location on the plant (to create spatially and temporally matched samples for comparison studies) were rapidly excised from plants and quick frozen in liquid nitrogen. Leaf tissue ground in the presence of liquid nitrogen with mortar/pestle was extracted. The foliar vitamin C content was determined by the ascorbate oxidase assay as previously described (Lorence et al., 2004). Briefly, tissue samples were harvested and immediately frozen in liquid nitrogen and stored at −80° C. till analysis. Samples were ground in 6% (w/v) meta-phosphoric acid, and centrifuged at 15,000×g for 10 min. Reduced vitamin C (a.k.a. ascorbate) was determined by measuring the decline in $A_{265}$ (extinction coefficient of 14.3 $cm^{-1}$ $mM^{-1}$) after addition of 1 unit of ascorbate oxidase (Sigma) to 1 mL of the reaction mix including tissue extract and 100 mM potassium phosphate (pH 6.9). Oxidized ascorbate (a.k.a. dehydroascorbate) was determined in a 1-mL reaction mixture including 1 μL of 20 mM dithiothreitol after incubating at room temperature for 20 min. Total AsA was the sum of reduced and oxidized AsA.

For enhancing the production of a particular target polypeptide of interest, optimization of the best time for antioxidant introduction into the system and the optimal antioxidant composition and concentrations will need to be determined. In some cases, the antioxidant(s) may function most appropriately when introduced prior to or subsequent to target polynucleotide or polypeptide activation or transfection of the construct encoding the target polypeptide. In other cases, both the antioxidant(s) and construct encoding the target polypeptide are co-delivered. In cases where elevated antioxidants are accomplished by genetic approaches that transfer genes directing increased production of antioxidants endogenously, the expression kinetics of the antioxidant-related polynucleotides may need to be optimized with respect to the kinetics of the target polypeptide. Variations in kinetics of gene expression of the antioxidant-related polypeptides and the target polypeptide can be accomplished using constitutive or inducible promoters and appropriate inducers such as those that are well known to those skilled in the art.

Using the methods described herein, target polypeptide production may be increased by at least 20%, 30%, 40%, 50%, 60%, 75%, 90%, 100%, 150%, 200% or more as compared to a control cell having no additional antioxidant. Suitably, the production of the target polypeptide may be increased by 2 fold, 4 fold, 6 fold, 8 fold, 10 fold or more after the antioxidant level in the cell is increased as compared to a control cell. A control cell may be a cell capable of expressing the target polypeptide, but not engineered to have increased antioxidant levels, a cell untreated or prior to treatment with a chemical antioxidant or a cell with an inducible antioxidant in the non-induced state. A control cell may also be a cell transient or stably expressing a second polypeptide that does not increase the antioxidant levels in the cell or transiently or stably transfected or transformed with an empty vector.

The examples taught herein, represent antioxidant-mediated enhanced yields of complex mammalian glycoproteins (such as IL-12) that are synthesized within the endomembrane system of a eukaryotic host cell. Additional embodiments may include target polypeptides that are synthesized within the cytosol, mitochondria or chloroplasts (plastids). The methods may be used to enhance synthesis of target polypeptides whose site of accumulation includes the nucleus, lysosomes, glyoxosomes, vacuoles, mitochondria, plastids, proteins bodies, endoplasmic reticulum (ER), membranes, and extracellular compartments including secretion into culture medium. In addition to increasing the total production of the target polypeptide, the resulting target polypeptide was also shown to be more stable and have higher activity than a target polypeptide produced in cells without increasing the level of antioxidant. As shown in the Examples, IL-12 and another glycoprotein were shown to be more stable, to maintain their functional conformation as measured by a conformation-sensitive ELISA assay, and to reduce oligomerization. Activity and stability may be increased if proteins are properly folded or are folded such that their secondary and tertiary conformations are stable.

Cells produced by the methods described herein and comprising elevated levels of at least one target polypeptide are also provided. In one embodiment, the cells may express more than one target polypeptide. For example, the cells may comprise polynucleotides encoding 1, 2, 3, 4, 5 or more target polypeptides. In one embodiment, the target polypeptides are related or perform an integrated function. The cells may comprise a first polynucleotide encoding a target polypeptide and a second polynucleotide encoding a second polypeptide capable of increasing antioxidants in the cell. The production of the second polypeptide allows increased production, stability or activity of the target polypeptide as compared to cells not expressing the second polypeptide. The cells may be within a multi-cellular system or a multi-cellular organism, such as a non-human animal or plant.

The target polypeptides produced by the methods disclosed herein may be used for a wide variety of purposes or in a variety of assays. Recombinant produced polypeptides (target polypeptides) may be used in a wide variety of clinical and industrial applications, including but not limited to industrial enzyme production, conversion and creation of biofuels, use in bioremediation, production of enzymes for use in food, paper, detergent, or textile production, enzymatic or antibody-based assays for medical diagnostics, and anti-microbials to name but a few of the potential uses of the target polypeptides produced by the methods described herein.

The cells expressing the target polypeptide may be directly administered to a subject with a condition responsive to the target polypeptide. In one embodiment, plant cells, plants or plant material (i.e. fruits, leaves, roots, seeds of the plant) may be fed directly to the subject in order to treat the condition or alleviate symptoms associated with the condition. In an alternative embodiment, the target polypeptide may be harvested from the cells and administered to the subject through any means known to those of skill in the art including, but not limited to, intranasally, mucosally, intradermally, parenterally, subcutaneously, orally, by aerosol or intramuscularly. Eye-drop administration or addition to food or water is additionally suitable. Conditions treatable by administration of a target polypeptide include but are not limited to an autoimmune disease, cancer, an infectious disease or the target polypeptide may be used as a vaccine antigen.

The target polypeptide may be harvested from the cells using any method including those available to those skilled in the art. Harvesting may include collecting a secreted fraction from the cells, tissues or organisms containing the target polypeptide (for example by centrifuging the cells and collecting the supernatant fraction) or making a crude preparation of the target polypeptide by breaking up the cells, but also includes isolating the target polypeptide from the cell in a more or less purified form. A crude preparation may include lysing the cells and separating the supernatant and the membrane fraction of the cells. The target polypeptide will be more abundant in one or the other fraction and can be used in downstream methods as a harvested target polypeptide. The target polypeptide may be further isolated or purified from the cells using standard biochemical techniques. The level of isolation or purification required will vary depending on the cell type used in the method, the target polypeptide and its downstream use or administration method.

A composition and method for increasing antioxidant levels in a cell transiently is also provided. The media composition includes water or a slightly acidic buffered solution and an antioxidant, suitably vitamin C or a vitamin C derivative. The antioxidant may be present in an amount ranging from 0.1 to 100 mM, suitably 1 to 50 mM, more suitably from 2 to 40 mM. The buffered solution is suitably a media in which the cell can survive, such as an isotonic or mildly hypotonic solution. For the plants and plant cells described herein the buffered solution is suitably comprised of 0.3-0.6× Murashige and Skoog basal medium salts, 0.7-1.2× MS vitamins, 1-8% sucrose, 0.7-1.2× benzylaminopurine. More suitably the buffer includes 0.5× Murashige and Skoog basal medium salts, 1× MS vitamins, 5% sucrose, 1× benzylaminopurine. The buffered solution may have an acidic pH, suitably the pH is between 4.0 and 7.0, more suitably the pH is between 5.0 and 6.5, more suitably the pH is between 5.5 and 6.0.

The following results are in support of the four general applications (see FIG. 1) wherein the increase of antioxidants in the selected bioproduction system leads to enhanced recombinant protein production in plants. The following data specifically addresses the application of this invention to plants however, its utility to other recombinant protein production platforms will not require undue experimentation for those familiar in the art.

The following examples based on a series of experimental data are offered by way of illustration and not by way of limitation. Any reference cited herein is hereby incorporated by reference in its entirety.

Examples

Materials and Methods
Plant Material

Four to five week-old *N. benthamiana* or *N. tabacum* plants were seeded on a standard PRO-MIX® BX with MYCORISE™ Pro soil (Premier Horticulture) and grown in an environmental growth chamber (Conviron) under controlled conditions as follows: 16 h light (12000-lux)/8 h dark, 65% relative humidity and a 25° C. (day)/21° C. (night) temperature cycle.

Bacterial Vectors for Plant-Based Protein Expression

Figure 2:
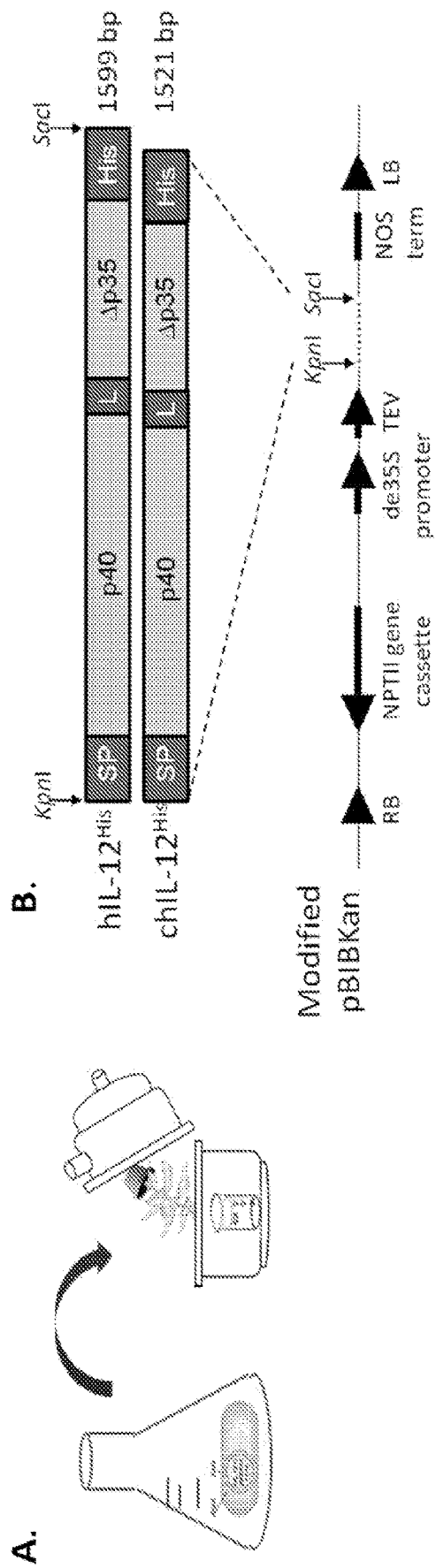
FIG. 2 is a graphic depiction showing the method of transiently transforming plants (FIG. 2A) and the model target polypeptide expression constructs used for doing so (FIG. 2B).

Human IL-12 (obtained from Dr Richard Mulligan's Lab, Children's Hospital Boston) and chIL-12 (synthesized and provided by BioStrategies LLC, Jonesboro, Ariz.) were developed that encode both subunits of the interleukin-12 as a single chain polypeptide separated with a gly-ser linker [$(G_4S)_3$; L] and tagged with a 6× histidine epitope (6×His) at the C-terminus as previously described (Medrano et al., 2010). See FIG. 2B. The hIL-12 and chIL-12 cassettes were introduced into KpnI and SacI restriction sites of the T-DNA region of a modified plant transformation/expression pBIB-Kan vector (Becker, 1990) providing the double-enhanced 35S promoter (de 35S-pro; Kay et al., 1987), a tobacco etch virus translational enhancer (TEV), and a plant gene terminator (NOS-ter) and mobilized into *Agrobacterium tumefaciens* strain LBA4404 using a modified freeze/thaw method (Holsters et al., 1978). See FIG. 2B. *A. tumefaciens* LBA4404 transformed with the pBIB-Kan "empty" vector was used as negative control (pBK).

Transient Infiltration

Transient infiltration was done according Medrano et al (2009), with some modifications as follows. Briefly, an *A. tumefaciens* inoculum integrated with the binary vector pBIB-Kan encoding IL-12 was cultured under standard conditions for 2 days at 28° C. The bacterial cultures were centrifuged and resuspended to a final $OD_{600}$ of 0.2-0.8, in 400 mL of a induction medium ("IM"; 0.5× Murashige and Skoog basal medium salts, 1× MS vitamins, 5% sucrose, 1× benzylaminopurine, 200 µM acetosyringone, pH 5.5). The cultures were incubated in 1M for ≥3 h at 28° C. Vacuum infiltration of 4-5-week-old *N. benthamiana* was accomplished by inverting a plant into a 400 mL glass beaker containing IM, ensuring that all leaves of the plant are immersed in the media. The beaker was placed in a vacuum desiccator unit (240-mm inner diameter) and using a vacuum pump, maximum pressure (~25 in. Hg) was applied for 2 min and then quickly released. Additional plants were subject to infiltration using the same construct/antioxidant culture, or replaced with a new beaker of IM containing another construct/antioxidant culture. A single IM culture was used for infiltrating typically 3 but up to 10 independent plants with no adverse effect on the amount of transgene product expressed and presence of exogenously introduced antioxidant in planta respectively. Infiltrated plants were returned to the environmental chamber at conditions established previously during plant growth. In the case of both model transgene constructs, leaves were harvested from plants at 48 h post-infiltration and stored at −80° C. for subsequent analyses.

Introduction of Antioxidants and Expression Constructs Into Plants by Vacuum Infiltration A fresh stock solution of vitamin C (AsA) (Sigma, St. Louis, Mo.) was prepared in distilled water and maintained on ice and covered with aluminum foil until use to limit potential degradation. Appropriate amounts of the AsA stock were added to a beaker containing the induction media (in the presence or absence of induced *A. tumefaciens* containing transgene expression construct) immediately prior to plant infiltration. The final concentration range of AsA we tested was 2-100 mM. Vitamin E and vitamin K were solubilized in chloroform and kept on amber tube on ice. The final concentration range of vitamins E and K tested were 5-100 µM.

Extraction of Leaf Tissue and Western Blotting

An initial test to quickly assess and compare the impact of various antioxidants on protein production involved protein extraction of the leaves using a standard SDS extraction buffer (150 mM Tris-HCl pH 6.8, 30% glycerol, 6% SDS, 5 mM EDTA pH 8.0) that solubilized all proteins. In the case of in planta AsA analysis, leaf tissues from defined location on the plant (to create spatially and temporally matched samples for comparison studies) were rapidly excised from plant and quick frozen in liquid nitrogen. For total soluble protein (TSP) determination, plant leaf tissues were extracted in a standard physiological extraction buffer such as phosphate buffer saline (PBS) or plant PBS to maintain protein conformation for in vitro analyses. The TSP of each sample was determined using a Standard Microplate Protocol according manufacture recommendation (Coomassie Bradford Protein Assay Kit, Pierce, Rockford, Ill.) and bovine serum albumin (BSA) was used for generating the standard curve.

Samples were resolved by SDS-PAGE (run under denaturing or reducing conditions) and Western immunoblotting analysis performed. For hIL-12 detection, primary antibody anti-human IL-12 (1:1000 v/v; R&D Systems) and secondary antibody anti-goat IgG-alkaline phosphatase conjugated (1:10,000 v/v; BIORAD®) was used. For chIL-12 detection, anti-6×His (C-term)-alkaline phosphatase conjugated (1:2000 v/v; Invitrogen) was used. Detection on immunoblots was carried out using the CDP-Star chemiluminescent substrate for alkaline phosphatase (Roche, Indianapolis, Ind.) and NitroBlock Enhancer II (Tropix Inc., Bedford, Mass.) in accordance with manufacturers' procedures. Densitometry using the BIORAD® VERSDOC4000™ and QUANT-1® software package was employed and relative protein expression was determined in order to evaluate the effect of antioxidants on plant-made protein expression.

ELISA For Quantitation of Recombinant IL-12 Proteins

The amount of hIL-12 expressed in *N. benthamiana* leaves in the presence or absence of modified antioxidants levels during bioproduction was quantitated using a commercially available heterodimer-specific hIL-12 enzyme-linked immunoabsorbant assay (ELISA) (R&D Systems). To assay hIL-12, leaves were ground in PBS buffer (137 mM NaCl, 2.7 mM KCl, 10.1 mM $Na_2HPO_4$, and 1.76 in $KH_2PO_4$ pH 7.0) at a 1:2 (w/v) ratio and supernatant extracts were analyzed by the ELISA. For hIL-12 detection, the ELISA used monoclonal antibodies specific for hIL-12 p70 for capture (0.2 µg/mL) and biotinylated anti-human IL-12 antibody for detection (4 µg/mL). Streptavidin-HRP (1:200 v/v) was used for chemiluminescence and 3,3',5,5'-tetramethylbenzidine (TMB; KPL) as a substrate for detection. Densitometry using the BIORAD® VERSDOC4000™ and QUANT-1® software package was employed and was established relative protein expression in order to evaluate the impact of antioxidants on its expression in plants.

Ascorbate Measurements

Foliar ascorbate content was determined by a microplate reader-based method described herein. Briefly, tissue samples were harvested and immediately frozen in liquid nitrogen and stored at −80° C. till analysis. Samples were ground in 6% (w/v) meta-phosphoric acid (Sigma), and centrifuged at 15,000×g for 10 min. Pellet was discarded and supernatant was collected for further analysis. Ascorbic oxidase (Sigma) was dissolved in 4 mM $Na_2HPO_4$, pH 5.6 containing 0.05% BSA at 40 U/mL and stored at −20° C. Reduced ascorbate was determined in a 300 µL reaction in triplicates by adding 275 µL of 0.1M of potassium phosphate buffer pH 6.9 into a 96-well plate (UV Flat Bottom Microplate, Thermo Scientific) containing 15 µL of sample supernatant. The mix was measured at $A_{265}$ and recorded. The decline in $A_{265}$ was measured after addition of 10 µL (1 U) of ascorbate oxidase (final concentration 0.0033 units of ascorbate oxidase, Sigma). A stable value was obtained after 1-2 min. Oxidized ascorbate was determined in a 300 µL reaction mixture including 275 µL of 0.1 M of potassium phosphate buffer pH 6.9 into a 96-well plate containing 15 µL of sample supernatant. The mix was measured at $A_{265}$ and recorded. Addition of 10 µL of 1.2 mM of dithiothreitol (DTT) with a final concentration of 40 µM of DTT (Sigma) were added and incubated at room temperature for 20 min. Total ascorbate was calculated as the sum of reduced and oxidized ascorbate, based on a standard curve with pure AsA (Sigma) run in parallel in the plate. $A_{265}$ was measure using a plate reader (model Power Wave XS, software KC Junior, Biotek).

In Situ $H_2O_2$ Detection

Staining for $H_2O_2$ in leaves which correlates with the presence of reactive oxygen species (ROS) is detected by an endogenous peroxidase-dependent staining procedure, using 3,3-diaminobenzidine (DAB). This assay provides a comparative in situ measure of the ROS levels in planta (Thordal-Christensen et al., 1997).

Results

The production of high levels of recombinant proteins in any given bioproduction system (e.g. plant, plant cell, animal cell, yeast, bacteria, algae) results in an increase in stress-related molecules. In the case of *Agrobacterium*-mediated infiltration of plants, not only is recombinant protein production itself stressful, but the mechanical assault on the host plant due to the act of vacuuming further contributes to the cellular stress levels in the system. As such, we targeted the transient plant expression system as an ideal model to initially test our hypothesis that promoting increased intracellular AsA levels and other antioxidants (vitamin E, K) coordinately with expression of our target proteins (hIL-12 and chIL-12) would increases the expression and accumulation of properly folded and active recombinant protein in plants.

Quantity and Quality of Recombinant Animal Proteins are Improved with Addition of Ascorbate to the Transient Plant Infiltration System.

Figure 3:
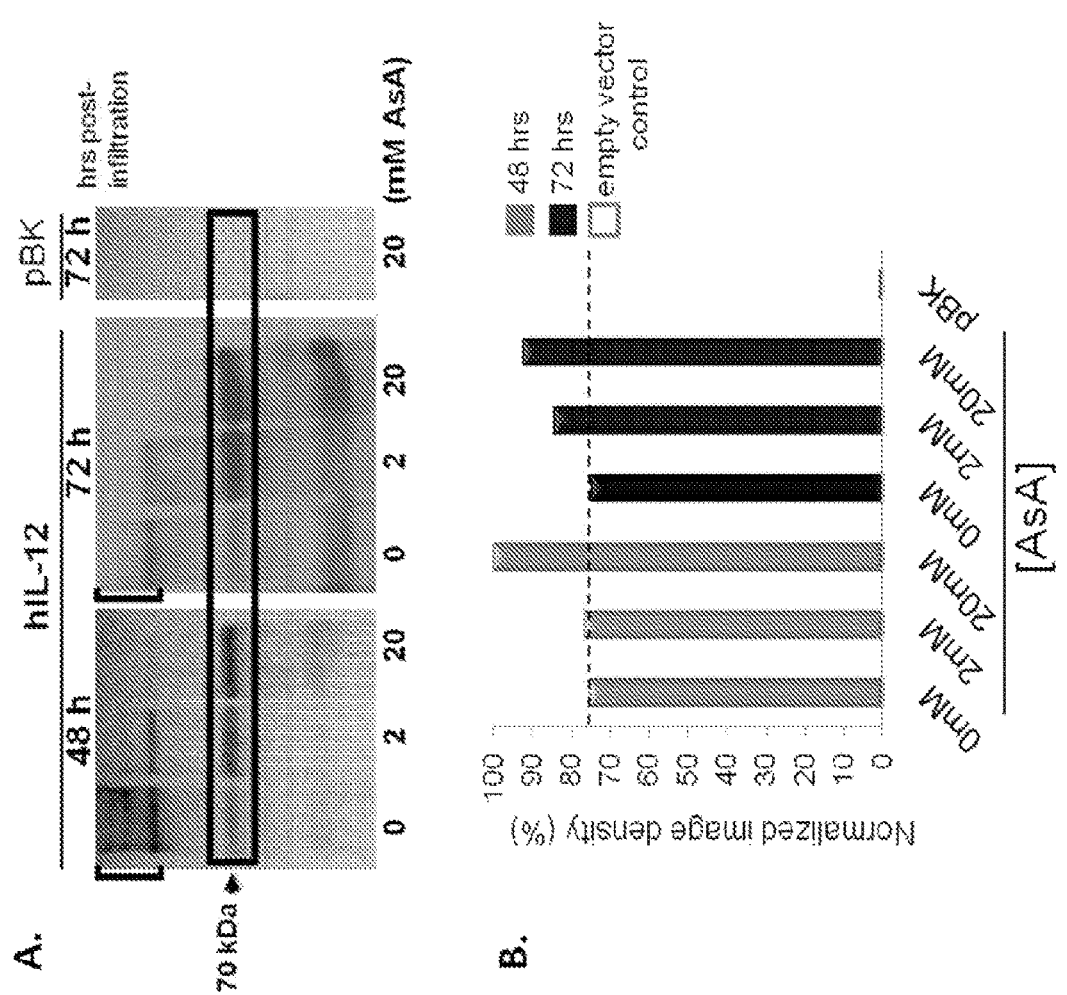
FIG. 3A is a photograph of a Western blot showing improved hIL-12 protein quantity and quality that is time and dose-dependent when vitamin C is introduced during the infiltration step of the transient plant expression system. Brackets highlight the region on the Western blot corresponding to the high molecular weight, oligomeric forms of hIL-12.
FIG. 3B is a graph showing the densitometric analysis of the Western blot. An approximate 25% increase in hIL-12 expression was seen in the presence of co-infiltrated vitamin C.

Using the *Agrobacterium*-mediated transient transformation method previously described (Medrano et al., 2009), 0, 2 and 20 mM of AsA were co-infiltrated with the hIL12 expression construct (FIG. 2; hIL-12:pBK) into *N. benthamiana* plants. Protein extracts from leaf tissue collected at 24, 48, 72 and 96 h post-infiltration were evaluated by anti hIL-12 Western immunoblot analysis. FIG. 3A illustrates that 20 mM co-infiltrated AsA resulted in a significant increase in monomeric, single-chain hIL12 relative to plants infiltrated with the hIL-12 expression construct alone. By semi-quantitative densitometry method we estimate a 25-30% increase in hIL-12 expression with inclusion of 20 mM AsA in induction medium FIG. 3B. pBIB-Kan (pBK), empty vector, used as a negative control showed no 70 kDa cross-reactive bands in the presence of AsA in the infiltration media. Interestingly, AsA sustained hIL-12 in planta for up to 72 h when the construct was co-infiltration of AsA compared to hIL-12 expressed in IM medium alone (0 mM AsA). In addition, the presence of AsA in the co-infiltrated media abrogates oligomer formation of hIL-12 observed in control plants (0 mM AsA) at both 48 and 72 h post-infiltration as denoted by the brackets in FIG. 3A. Taken together, this data suggests that attaining increased intracellular AsA levels prior to expression of our target model protein may provide a more favorable redox environment both in the cytosol and the ER that result in the observed increase in expression and accumulation of properly folded and active recombinant hIL-12 in plants.

Figures 4, 4A, 4B:
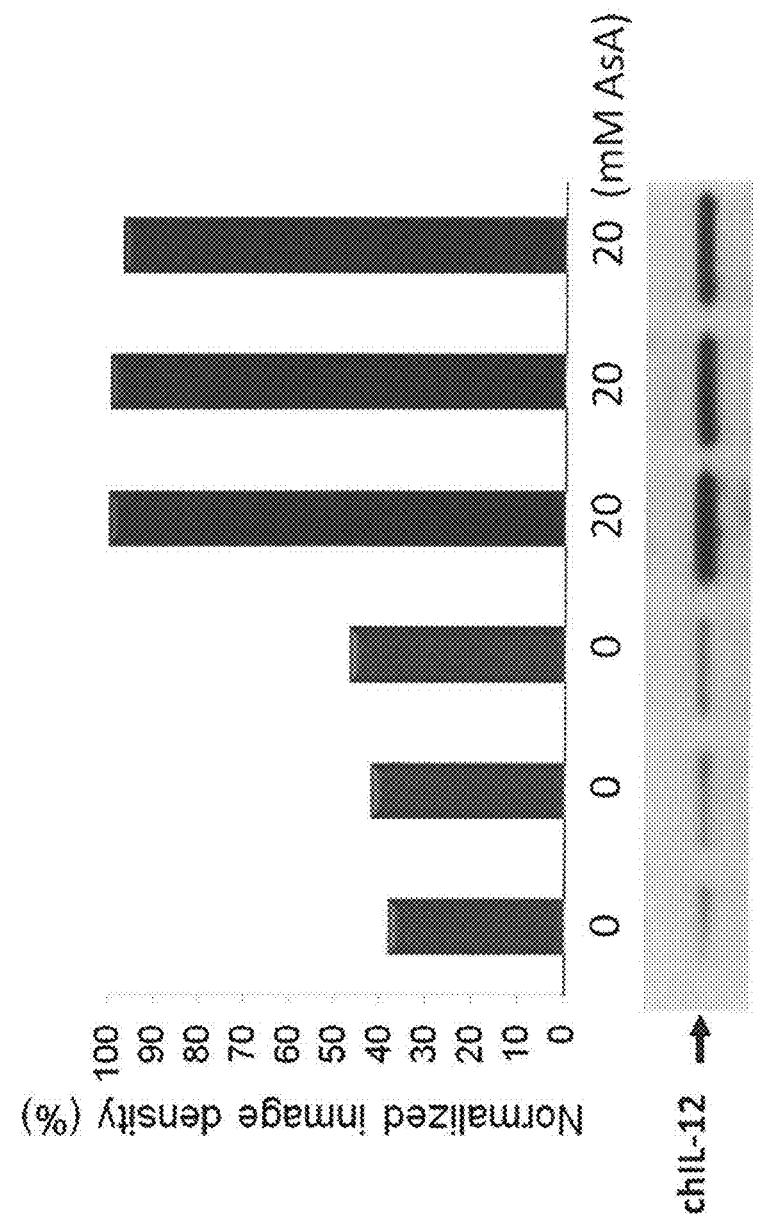
FIG. 4 is a photograph of a Western blot (FIG. 4B) and semi-quantitative densitometry analysis (FIG. 4A) showing increase of another protein, chIL-12, when expressed in plants using the transient system and co-infiltration of vitamin C.

To establish that this positive effect observed with infiltrated AsA on hIL-12 protein expression levels was not protein and/or construct specific, a second protein was tested. The chicken homolog of IL-12 (chIL-12) while exhibiting "classic" IL-12 activity, (i.e., stimulation of interferon-gamma secretion, and presumed binding to its cognitive receptor) in fact only shares ~34% sequence homology with its mammalian homolog and thus presents as a distinct and unique protein. The chIL-12:pBK expression construct was vacuum infiltrated into *N. benthamiana* plants using the transient system in the presence and absence of 20 mM AsA. See FIG. 2. At 48 h post-infiltration, leaves were collected, total protein extracted and evaluated on an anti-his antibody Western blot. See FIG. 4B. On average an approximate 3-fold increase in chIL-12 protein expression was observed when expressed in the presence of 20 mM AsA (FIG. 4A). This data further validates the positive impact of AsA actively delivered (in this case via vacuum infiltration) into host protein production cells on recombinant protein expression is protein independent.

Additional protein constructs including a large 94 kDa human glycoprotein also benefited from the addition of AsA into the plant transient bioproduction system. As shown in FIG. 5, the presence of 20 mM co-infiltrated AsA was shown to enhance the in planta accumulation of a complex human glycoprotein of therapeutic importance. While 48 hrs post-infiltration shows similar expression for +/− co-infiltrated AsA, the stable accumulation of this protein is enhanced in the presence of AsA during infiltration of the transgene expression construct at 72 hrs post-infiltration. Thus, the half life of this protein was markedly enhanced up to 72 hrs post-infiltration relative to its expression in the absence of this antioxidant (FIG. 6).

Dose-Dependency of Co-Infiltrated AsA in Transient Transformation System

To establish the effective dosage of infiltrated AsA into the system and define the kinetics of this antioxidant on recombinant protein expression in the transient expression platform, increasing concentrations of AsA were added to the infiltrate medium at 0, 20, 40, 60 mM AsA and co-introduced into the N. benthamiana plant with the hIL-12:pBK expression construct. A hIL-12 western blot and semi-quantitative densitometry analysis illustrated in FIG. 6A shows a clear dose dependent increase in hIL-12 protein expression levels through 60 mM AsA. Leaves of host plants infiltrated with 80 mM AsA began to show signs of necrosis and significant necrotic lesions at 100 mM AsA. To date the results of AsA dose-response studies in the plant transient infiltration model suggest 20-60 mM AsA concentrations is an effective dose range in promoting a favorable recombinant protein yield.

In the same AsA dose-response experiment, we measured the impact of increased cellular levels of AsA on the overall protein synthetic capacity of the host plant. FIG. 6B showed that AsA increased the total soluble protein levels in 48 h post-infiltrated plant leaves again in a dose-dependent manner. This result suggests that the overarching effect of AsA on the plant recombinant expression system not, only favors increased recombinant protein expression but boosts the entire protein production capacity of the plant. To confirm that this increase in recombinant protein expression due to the presence of elevated AsA present in the plant cell also impacted the overall protein biosynthetic machinery in the plant, total foliar AsA concentrations in the transient system host plants was measured. Concomitant with increased protein expression, the same dose-dependent increase in planta foliar AsA levels was observed (FIG. 7A). A second method and visual confirmation that transient AsA introduction effectively increased the level of antioxidant status in host plants was shown using a DAB assay (Thordal-Christensen et al., 1997). In this assay (FIG. 7B), in situ hydrogen peroxide ($H_2O_2$) production, the main form of reactive oxygen species (ROS) in leaf tissues, showed browning regions in the 0 mM AsA infiltrated plant leaves. As the exogenously added. AsA was increased from 20 to 60 mM, the presence of $H_2O_2$ staining was minimal in plant leaves correlating with lower levels of ROS present. While some staining at 80 mM AsA was observed, this brown staining was clearly detectable at 100 mM AsA suggesting that higher levels of antioxidant resulted in toxicity to the plant. Taken together this data defines the effective dose in promoting a healthy plant phenotype while maximizing recombinant protein production is 20-60 mM AsA in the plant transient infiltration system.

Co-Infiltrated Lipophilic Antioxidants Promote Similar Increases in Recombinant Protein Expression.

Additional plant antioxidants were evaluated for their capacity to mediate an effect on protein expression levels in planta similar to that observed for AsA. The lipophilic nature of vitamins E and K predicted that their cellular location and possible role in recombinant protein production may in fact be distinct from that of the water-soluble AsA. Many of the recombinant proteins of interest expressed in plants are targeted to the endomembrane system further highlighting the possible importance of these lipophilic vitamins in recombinant protein expression in plants. Furthermore, as two of the most abundant lipophilic antioxidants they have been shown to be key redox molecules in maintaining ER homeostasis in mammalian systems (Bánhegyi et al., 2007). Therefore, vitamins E and/or K may play a key role for ensuring sustained ER health in the host plant during the strenuous bioproduction process that in turn leads to improved recombinant protein quality and quantity.

Figure 8:
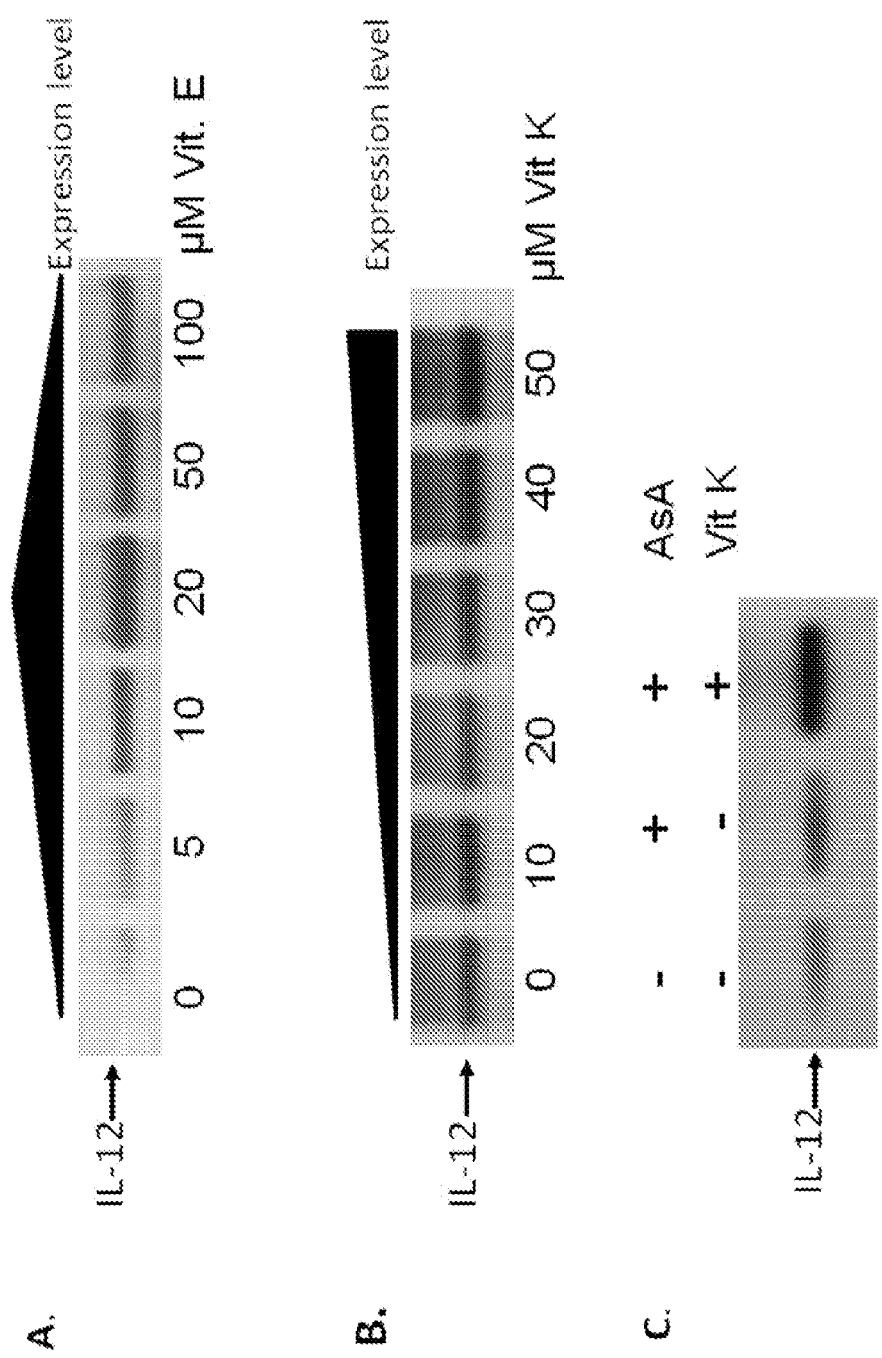
FIG. 8A is a photograph of a Western blot showing impact on chIL-12 protein production when various doses of co-infiltrated vitamin E are used in the transient plant expression system.
FIG. 8B is a photograph of a Western blot showing impact on hIL-12 protein production when increased concentrations of co-infiltrated vitamin K are used in transient plant expression system.
FIG. 8C is a photograph of a Western blot showing the impact of co-infiltrating with multiple antioxidants—vitamin E and vitamin C—on hIL-12 protein production in the transient plant system.

Dose-response studies with these antioxidants indicated that increasing vitamin E concentrations in the infiltration medium showed the greatest impact in transient chIL12 protein expression at 20 μM with in fact reduced improvement in protein production at higher vitamin E concentrations (50-100 μM; FIG. 8A). In addition, 100 μM vitamin E appeared to be toxic to the plant. Conversely, in the case of transient plant expression of hIL-12, vitamin E alone had no effect on expression. Co-infiltration of μM range of vitamin K delivered similar dose kinetic trends as observed with AsA for hIL-12, suggesting that lipophilic antioxidants can increase production of hIL-12 as well (FIG. 8B). Based on these pleotropic activities of water and fat soluble vitamins, we were interested in determining if introduction of multiple antioxidants would have additive or synergistic effects on the transient protein expression in plants. The Western blot in FIG. 8C represents co-infiltration of vitamin E and AsA. Surprisingly, co-infiltration resulted in an increased expression of hIL-12 protein levels above that of AsA alone. In the case of vitamin E, synergy with AsA may be explained due to AsA's role in "recycling" oxidized vitamin E back into its reduced state.

Enhancing in Planta AsA Levels Favorably Impacts Recombinant Protein Recovery

Figure 9:
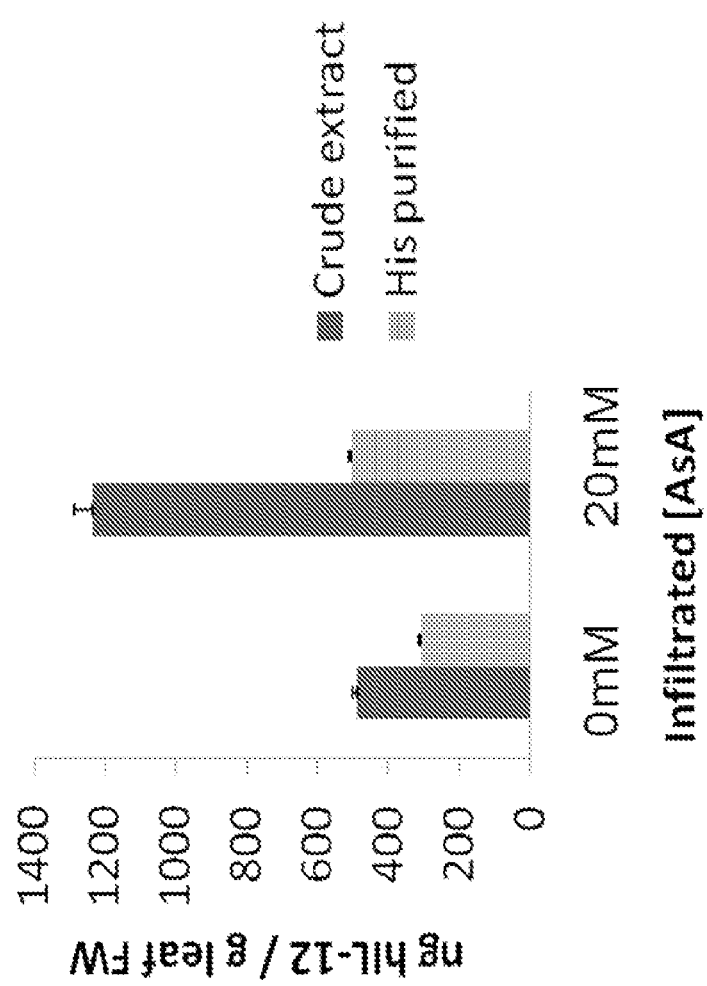
FIG. 9 is a graph showing that the addition of vitamin C also enhances recovery of purified active hIL-12 using an ELISA specific for IL-12.

Finally while increased expression and accumulation of complex animal proteins in plants is suggestive of increased recombinant product, the recovery of purified product is the true measure for the success of increased antioxidant to the transient plant expression system. As shown in FIG. 9, AsA indeed allowed recovery of higher amounts of bioactive hIL12 protein that aligned with the increased protein production/accumulation of hIL-12 shown in FIG. 6. The presence of 20 mM exogenously added AsA to the system recovered approximately 20-25% more product when compared to expression in the absence of the antioxidant which is significant in consideration of scaled recombinant protein production.

Figure 10:
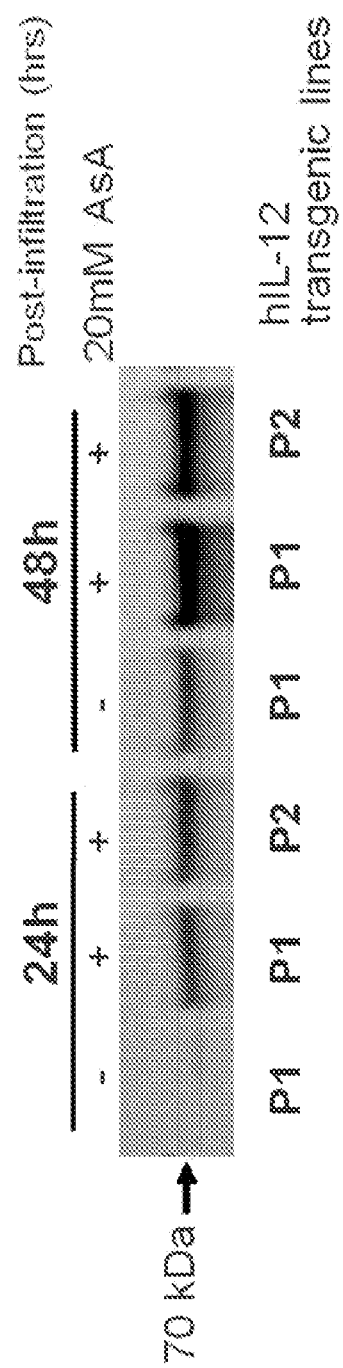
FIG. 10 is a photograph of a Western blot showing the impact of infiltrated vitamin C on human IL-12 protein levels of stable transgenic *Nicotiana tubacum* plant lines.

Antioxidants Impact the Production of hIL-12 Expressed in Stable Transgenic Plants Stable N. tabacum lines engineered to stably express hIL-12 protein were vacuum infiltrated with AsA in IM media and leaves were collected 24 and 48 h post-infection. A hIL-12 Western blot in FIG. 10 showed that infiltrated AsA was also capable of increasing the overall expression of hIL-12 protein levels where a transgene is stably integrated and expressed under a strong constitutive promoter. This finding further supports the concept that increasing the antioxidant capacity of the host plant enhances the overall biosynthesis of the plant in serving as a factory for recombinant protein production.

Antioxidant Levels May Also be Increased in Stable Transgenic Lines

Figure 11:
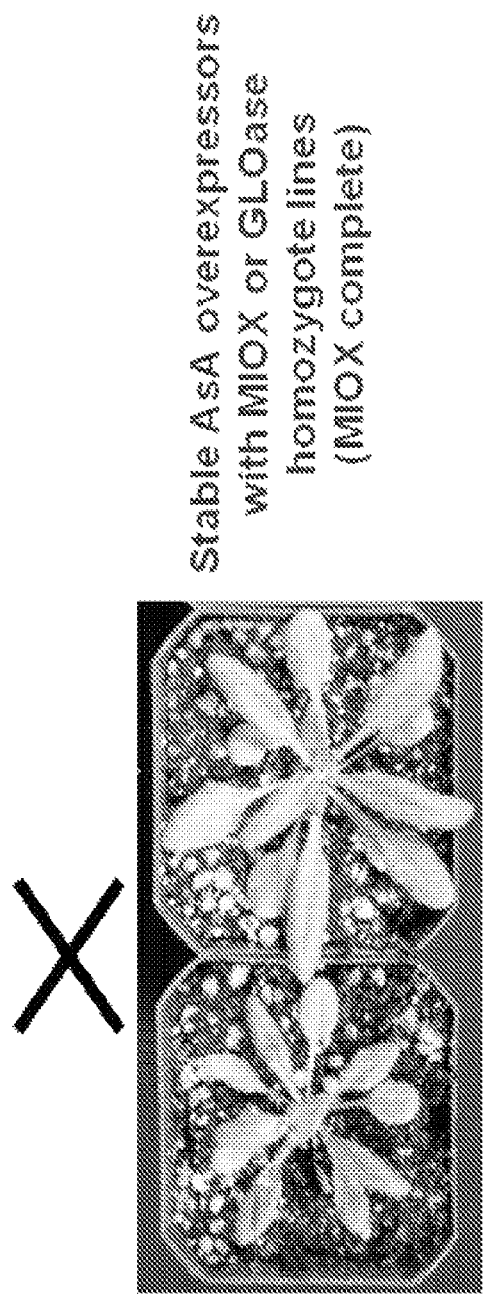
FIG. 11 is a photograph showing an *Arabidopsis* plant line stably expressing hIL-12 and another stably over-expressing myo-inositol oxygenase 4 (MIOX4), a gene in the vitamin C biosynthetic pathway, and over-expressing vitamin C.

Arabidopsis plant lines over-expressing enzymes in the AsA synthetic pathway have been developed for improved recovery of recombinant hIL-12 protein in stable transgenics. Homozygote Arabidopsis plant lines over-expressing an AsA pathway biosynthetic enzyme, MIOX4 have been developed and we are in the process of generating homozygous plant lines over-expressing the GLOase enzyme. See FIG. 11. Both enzymes are involved in AsA synthesis and over-expression of either has been shown to result in increased AsA synthesis (Radzio et al., 2003 and Lorence et al., 2004). The MIOX4 plant lines with enhanced production of AsA are being crossed with *Arabidopsis* lines stably expressing the hIL-12 model recombinant protein to form double transformant stable lines. See FIG. 11. We expect that these double transformant plant lines will express increased AsA and produce an increased amount of hIL-12 as compared cohort plants transgenic for only hIL-12. These plants will validate the stable transgenic approach to improving host plant fitness for increased expression of a transgene.

Rice cells can also be genetically engineered to express higher levels of AsA and concomitantly higher levels of recombinant proteins. As shown in FIG. 12A, expression cassettes encoding the *Arabidopsis* MIOX4 or the rat GLOase transgene were inserted into the T5 locus of a rice cell culture line using a Cre-loxP integration strategy. The resulting rice cells produced increased amounts of MIOX4 as compared to wild-type cells. See inset Western blot in FIG. 12B. In FIG. 12B, the amount of AsA produced by several different lines is shown. The AsA content for several of the lines was 2-4 fold higher than that of control rice cells. As in the case with the *N. benthamiana* transiently infiltrated with vitamin C, these rice cell lines are predicted to have increased TSP levels.

These cells will be used to stably transfect a target polypeptide such as IL-12. We expect that the production of IL-12 will be higher in the double-transgenics than in the control cells. The cells may be used to make plant lines that may be administered to treat a disease or condition responsive to administration of the target polypeptide. Alternatively, the target protein may be harvested from the cells for use in a variety of potential applications.

Transgenic rice plants can also be genetically engineered to express higher levels of AsA and concomitantly higher levels of recombinant proteins. As shown in FIG. 13, transgenic plant lines encoding the *Arabidopsis* MIOX4 or the rat GLOase transgenes were established in both the Taipei and Nipponbare rice cultivar backgrounds by particle bombardment. The amount of foliar AsA in several different rice transgenic plant lines is compared in FIG. 13. These plants will be used to stably express a target polypeptide such as IL-12. We expect that the production of IL-12 will be higher in the double-transgenics than in the control plants. These rice plants are expected to have increased TSP levels. The plants may be administered to treat a disease or condition responsive to administration of the target polypeptide. Alternatively, the target protein may be harvested from the plants for use in a variety of potential applications.

REFERENCES

Bánhegyi G, Benedetti A, Csala M, Mandl J (2007) Stress on redox. *FEBS Lett.* 581: 3634-3640.

Becker, D. (1990) Binary vectors which allow the exchange of plant selectable markers and reporter genes. *Nucleic Acids Res.* 18, 203.

Holsters, M., de Waele, D., Depicker, A., Messens, E., Van Montangu, M., and Schell, J. (1978) Transfection and transformation of *A. tumefaciens*. *Mol. Gen. Genet.* 163, 181-187.

Joh L D, Wroblewski T, Ewing N N, and VanderGheynst J S (2005) High-level transient expression of recombinant protein in lettuce. *Biotechnol. Bioeng.* 91:861-71.

Kapila J, DeRycke R, VanMontagu M, Angenon G. (1997) An *Agrobacterium*-mediated transient gene expression system for intact leaves. *Plant Sci* 122:101-108.

Kay, R., Chan, A., Daly, M., and McPherson, J. (1987) Duplication of CaMV 35S promoter sequences creates a strong enhancer for plant genes. *Science* 236, 1299-1303.

Lisko K A, Harris R S, Yactayo-Chang J and Lorence, A (2008) Engineering ascorbate for enhanced growth, nutritional content, and stress tolerance in crops. *In Vitro Cell. Develop. Biol. Animal* 44: S28.

Lorence A, Mendes P, Chevone B I, and Nessler C L (2004) myo-Inositol Oxygenase Offers a Possible Entry Point into Plant Ascorbate Biosynthesis. *Plant Physiol.* 134: 1200-1205.

Medrano G, Reidy M J, Liu J, Ayala J, Dolan M C, and Cramer C L (2009) Rapid system for evaluating bioproduction capacity of complex pharmaceutical proteins in plants In: "Recombinant Proteins from plants", Methods and Protocols. Series: Methods in Molecular Biology. L. Faye, and V. Gomord, eds. Humana Press, Totowa, N.J., 483:51-67.

Medrano, G., Dolan, M. C., Stephens, N. T., McMickle, A., Erf, G., Radin, D. and Cramer, C. L. (2010) Efficient plant-based production of chicken IL-12 yields a strong immunostimulatory cytokine. *J. Interferon Cytokine Res.* 30(3), 21-31.

Radzio J, Lorence A, Chevone B I, and Nessler C L (2003) L-Gulono-1,4-lactone Oxidase Expression Rescues Vitamin C Deficient *Arabidopsis* (vtc) Mutants. *Plant Molec. Biol.* 53: 837-844.

Sainsbury F and Lomonossoff G P (2008) Extremely High-Level and Rapid Transient Protein Production in Plants without the Use of Viral Replication. *Plant Physiol.* 148:1212-1218.

Schillberg S, Twymanb R M, and Fischer R (2005) Opportunities for recombinant antigen and antibody expression in transgenic plants—technology assessment. *Vaccine* 23: 1764-1769.

Thordal-Christensen H, Zhang Z, Wei Y, Collinge D B (1997) Subcellular localization of $H_2O_2$ in plants. $H_2O_2$ accumulation in papillae and hypersensitive response during the barley-powdery mildew interaction. *Plant J.* 11:1187-1194.

Zhang W, Lorence A, Gruszewski H A, Chevone B I and Nessler C L (2009) AMR1, an *Arabidopsis* gene that coordinately and negatively regulates the mannose/L-galactose ascorbic acid biosynthetic pathway. *Plant Physiol.* 150: 942-950.

We claim:

1. A method of increasing production of a target polypeptide in a plant cell, the method comprising:
co-introducing Vitamin C and a first polynucleotide encoding the target polypeptide into the cell using a transient infiltration or delivery system selected from the group consisting of vacuum infiltration, liposome mediated delivery, sonication, temperature (heat) shock, particle bombardment, electroporation, reversible membrane permeabilization, and microinjection to produce the cell comprising the first heterologous polynucleotide encoding the target polypeptide, wherein both the Vitamin C and polynucleotide encoding the target polypeptide are co-delivered,
wherein the Vitamin C is added at 20 mM to 60 mM, and
wherein the increased level of Vitamin C in the cell increases the production of the target polypeptide and reduces the formation of multimers of the target polypeptide as compared to the production of the target polypeptide in a control cell without increased Vitamin C.

2. The method of claim 1, wherein the plant cell is a from a plant of the genus *Nicotiana*.

3. The method of claim 1, additionally comprising increasing the level of a lipophilic antioxidant in the cell.

4. The method of claim 1, wherein the first polynucleotide encoding the target polypeptide is being stably integrated into the genome of the cell.

5. The method of claim 1, wherein the target polypeptide is transiently expressed by the cell.

6. The method of claim 1, wherein the target polypeptide is an antibody, an interleukin, a growth factor, an enzyme, a cytokine, or a therapeutic polypeptide.

7. The method of claim 1, wherein the target polypeptide requires post-translational processing for activity.

8. The method of claim 1, wherein Vitamin C is added at a concentration of 40 mM to 60 mM.

9. The method of claim 3, wherein the lipophilic antioxidant is added at a concentration of 10 µM to 100 µM.

10. The method of claim 1, further comprising harvesting the target polypeptide from the cell.

11. The method of claim 9, wherein the lipophilic antioxidant is vitamin K or vitamin E.

\* \* \* \* \*